(12) United States Patent
Klein et al.

(10) Patent No.: US 9,296,551 B2
(45) Date of Patent: Mar. 29, 2016

(54) FLUID CARTRIDGE AND DISPENSION DEVICE

(75) Inventors: Thomas Klein, Kindberg (AT); Andreas Zimmer, Graz (AT); Martin Trinker, Graz (AT); Peter Brunner, Ismaning (DE); Bernd Heiko Lindena, Westendorf (AT); Rainer Behne, Dubai (AE)

(73) Assignee: Medic Activ Vertriebs GmbH, Grunwald (DE)

( * ) Notice: Subject to any disclaimer, the term of this patent is extended or adjusted under 35 U.S.C. 154(b) by 85 days.

(21) Appl. No.: 14/241,809

(22) PCT Filed: Aug. 24, 2012

(86) PCT No.: PCT/EP2012/066520
§ 371 (c)(1),
(2), (4) Date: Feb. 27, 2014

(87) PCT Pub. No.: WO2013/030117
PCT Pub. Date: Mar. 7, 2013

(65) Prior Publication Data
US 2014/0212334 A1    Jul. 31, 2014

(30) Foreign Application Priority Data
Aug. 31, 2011    (EP) .................................... 11179621

(51) Int. Cl.
*B01D 11/04*    (2006.01)
*B01D 11/02*    (2006.01)
(Continued)

(52) U.S. Cl.
CPC ............. *B65D 83/66* (2013.01); *A61M 11/002* (2014.02); *A61M 11/06* (2013.01);
(Continued)

(58) Field of Classification Search
CPC ............... A61L 2/00; A61L 2/18; B67D 1/00
USPC ........... 422/28, 256, 261, 292, 300; 222/129; 221/92, 287; 220/694
See application file for complete search history.

(56) References Cited

U.S. PATENT DOCUMENTS

2007/0074722 A1    4/2007    Giroux et al.
2007/0107725 A1    5/2007    Addington et al.

FOREIGN PATENT DOCUMENTS

DE    WO 2011/082838 A1 *    7/2011    ............. A61H 33/06
EP    1 806 157 A2    7/2007
(Continued)

OTHER PUBLICATIONS

European English Translation of WO 2011/082838 A1.*
(Continued)

*Primary Examiner* — Monzer R Chorbaji
(74) *Attorney, Agent, or Firm* — Lewis Roca Rothgerber Christie LLP

(57) ABSTRACT

A fluid cartridge (100) for dispensing a fluid, the fluid cartridge (100) comprising a casing (102) for accommodating the fluid, a pressure feed interface (104) configured for being coupled to a pressure feed unit (106) for feeding the fluid in the casing (102) with pressurized medium, a fluid dispensing unit (108) configured for generating particles, particularly fluid particles, upon feeding the fluid in the casing (102) with pressurized medium, and a fluidic path (110) in the casing (102) being opened or openable for enabling the particles, particularly fluid particles, to leave the casing (102) through the fluidic path (110).

22 Claims, 19 Drawing Sheets

(51) Int. Cl.
- A61L 2/00 (2006.01)
- B67D 5/60 (2006.01)
- B65G 29/00 (2006.01)
- B65D 25/00 (2006.01)
- B65D 83/66 (2006.01)
- A61M 11/06 (2006.01)
- B05B 7/00 (2006.01)
- B05B 1/26 (2006.01)
- B05B 7/16 (2006.01)
- B05B 7/24 (2006.01)
- B05B 15/06 (2006.01)
- B65D 83/30 (2006.01)
- B65D 83/72 (2006.01)
- B65D 83/14 (2006.01)
- A61M 11/00 (2006.01)
- A61M 15/00 (2006.01)
- A61M 16/10 (2006.01)
- B05B 1/36 (2006.01)
- B05B 11/00 (2006.01)
- B05B 15/12 (2006.01)

(52) U.S. Cl.
CPC ........ *A61M 15/0043* (2014.02); *A61M 16/108* (2014.02); *B05B 1/265* (2013.01); *B05B 7/0012* (2013.01); *B05B 7/1626* (2013.01); *B05B 7/2405* (2013.01); *B05B 15/065* (2013.01); *B65D 83/303* (2013.01); *B65D 83/72* (2013.01); *B65D 83/753* (2013.01); *A61M 2202/0208* (2013.01); *A61M 2205/6054* (2013.01); *A61M 2205/6063* (2013.01); *A61M 2205/6072* (2013.01); *B05B 1/36* (2013.01); *B05B 11/0054* (2013.01); *B05B 15/12* (2013.01)

(56) References Cited

FOREIGN PATENT DOCUMENTS

| | | |
|---|---|---|
| WO | WO 2006/084543 A1 | 8/2006 |
| WO | WO 2009/087053 A1 | 7/2009 |
| WO | WO 2011/082838 A1 | 7/2011 |

OTHER PUBLICATIONS

International Search and Written Opinion of corresponding PCT/EP2012/066520, dated Feb. 28, 2013, 19 pages.

* cited by examiner

FLUID CARTRIDGE AND DISPENSION DEVICE

This application is a National Phase Patent Application and claims priority to and benefit of International Application Number PCT/EP2012/066520, filed on Aug. 24, 2012, which claims priority to and the benefit of European Patent Application Number 11179621.5, filed on Aug. 31, 2011, the entire disclosures of which are incorporated herein by reference.

The invention relates to a fluid cartridge.

Moreover, the invention relates to a method of operating a fluid cartridge.

Furthermore, the invention relates to a dispension device.

Moreover, the invention relates to a method of operating a dispension device.

Beyond this, the invention relates to an arrangement.

Furthermore, the invention relates to a method of use.

For wellness, human medical and veterinary applications, it may be necessary to dispense materials such as physiologically active fluids.

WO 2009/087053 discloses a method and a device for atomizing at least one fluid, in particular for producing a therapeutically effective aerosol in a treatment room, wherein a fluid to be atomized is supplied with pressurized medium and is discharged into the treatment room through a nozzle in the form of small particles at a flow rate in the region of 50 to 300 m/s. The device comprises at least one aerosol generator for discharging an aerosol, wherein the aerosol generator supplies a fluid to be atomized with pressurized medium and discharges it at a flow rate in the region of 50 to 300 m/s through at least one outlet opening in the form of small particles into a treatment room.

WO 2011/082838 discloses a method and a device for generating a nanoaerosol, wherein at least one fluid to be atomized is atomized in a nozzle via a nozzle opening of the nozzle along an outlet direction in the form of fluid particles, the atomized fluid particles are diverted from the outlet direction and larger fluid particles are at least partially separated from smaller fluid particles, the separated larger fluid particles are returned to the fluid to be atomized and the smaller fluid particles are emitted to the environment. A cartridge in which the nozzle and the fluid to be atomized are arranged is used. A stream of a carrier gas is generated in the nozzle and at least one fluid to be atomized is brought into contact with the carrier gas.

It is an object of the invention to provide an efficient way of dispensing a fluid.

In order to achieve the object defined above, a fluid cartridge, a method of operating a fluid cartridge, a dispension device, a method of operating a dispension device, an arrangement, and a method of use according to the independent claims are provided.

According to an exemplary embodiment of the invention, a fluid cartridge for dispensing (particularly nebulizing or atomizing) a fluid (particularly a gas and/or liquid, optionally including a solid additive) is provided, wherein the fluid cartridge comprises a casing for accommodating the fluid (for instance in a fluid-tight manner), a pressure feed interface configured for being coupled to at least one (i.e. to one pressure feed unit or to a plurality of pressure feed units) pressure feed unit (particularly of a dispenser device) for feeding the fluid in the casing with pressurized medium (particularly a gas and/or liquid under overpressure, particularly pressurized air or oxygen), a fluid dispensing unit configured for generating particles (particularly fluid particles, however pure solid particles are possible as well) upon feeding the fluid in the casing with pressurized medium, and a fluidic path in the casing being opened or openable for enabling the particles (particularly fluid particles, more particularly in the form of an aerosol, even more particularly in the form of a nanoaerosol) to leave the casing (or to propagate out of the casing, i.e. the particles are emitted to the environment) through the fluidic path.

According to another exemplary embodiment of the invention, a method of dispensing a fluid is provided, wherein the method comprises accommodating the fluid in a casing, coupling a pressure feed interface of the casing to a pressure feed unit to thereby feed the fluid in the casing with pressurized medium, generating particles (particularly fluid particles) in the casing upon feeding the fluid in the casing with pressurized medium, and providing a fluidic path in the casing being open for enabling the particles to leave the casing through the fluidic path.

According to still another exemplary embodiment of the invention, a dispenser device for dispensing a fluid from a fluid cartridge (which may be a fluid cartridge having the above mentioned features) is provided, the dispenser device comprising a cartridge accommodation unit configured for accommodating the fluid cartridge, a pressure feed unit configured for feeding the fluid in a casing of the fluid cartridge with a pressurized medium upon accommodating the fluid cartridge in the cartridge accommodation unit to thereby generate particles (particularly fluid particles) leaving the casing through a fluidic path in the casing upon feeding the fluid in the casing with the pressurized medium.

According to another exemplary embodiment of the invention, a method of dispensing a fluid from a fluid cartridge is provided, wherein the method comprises accommodating the fluid cartridge in a cartridge accommodation unit, and feeding the fluid in the casing with a pressurized medium upon accommodating the fluid cartridge in the accommodation unit to thereby generate particles (particularly fluid particles) leaving the casing upon feeding the fluid in the casing with the pressurized medium.

According to still another exemplary embodiment of the invention, an arrangement for dispensing a fluid is provided, wherein the arrangement comprises a fluid cartridge having the above mentioned features and accommodating the fluid, and a cooperating dispenser device having the above mentioned features and being configured for dispensing the fluid from the fluid cartridge.

According to yet another exemplary embodiment of the invention, an arrangement having the above mentioned features is used for treating a physiological subject (such as a human being or an animal, particularly a horse or a falcon) by the dispensed fluid (or by the generated particles, particularly fluid particles). The dispensed fluid may particularly be a non-medical preparation (i.e. may be free of any medication, for instance may be a fluid for wellness applications or cosmetic applications). Alternatively, the dispensed fluid may be a medical preparation (i.e. may comprise a pharmaceutically active agent).

According to an exemplary embodiment, a pressurized carrier fluid is supplied to a fluid (particularly a liquid) accommodated in a casing to thereby bring the fluid into motion. Particles (particularly fluid particles) will disrupt from the liquid surface and may be forced against an abutting surface of the fluid cartridge to thereby atomize or vaporize. Relatively large particles will then, under the influence of gravitation, propagate back to the liquid surface, whereas smaller particles such as nanoparticles will be capable of moving through one or more openings in the casing towards an environment. Therefore, the liquid (which may be a wellness preparation or a physiologically active substance) will be dispensed in nanoparticles towards the environment.

In the following, further exemplary embodiments of the fluid cartridge will be explained. However, these embodiments also apply to the method of operating a fluid cartridge, the dispension device, the method of operating a dispension device, the arrangement, and the method of use.

In an embodiment, the casing, particularly including a Venturi nozzle of the casing, is made by injection molding, particularly may be made by four injection molding parts. Hence, the Venturi principle of atomizing liquid into finest particles has been adapted to a casing made purely by injection molding, i.e. with very low cost. Embodiments of the invention hence relate to a casing which is constituted by four cooperating parts or members each of which being manufacturable with the economic method of injection molding. Nevertheless, a powerful vaporization of liquid can be achieved with such a casing even under the harsh conditions of a high pressure (for instance 2 bar) of the pressurized medium in combination with requirements of sterile conditions of the fluid to be dispensed or dispersed.

In an embodiment, the casing comprises a bottom part and a top part, the bottom part and the top part being integrally connected to one another, particularly in a hermetically sealed fluid-tight manner and/or in a sterile manner. The bottom part and the top part can both be manufactured by injection molding, can be assembled (particularly together with two further injection molding parts) and can be sealed so that no fluid, particularly liquid, may pass through the connected top part and bottom part. Therefore, the liquid can be kept within the casing in a sterile way, wherein sterility can be maintained over the entire lifetime of the casing.

Particularly, the fluid cartridge can be configured as a single use device or disposable device which is used until the liquid contained therein is empty and is then thrown away. Therefore, sterility can be guaranteed which could not be guaranteed upon refill of an already used casing by a user. After an aseptic filling of the fluid cartridge the interior of the fluid cartridge remains sterile through all procedural steps. Alternatively, the fluid cartridge with its casing may be reused. In such a scenario, it is advantageous to sterilize or autoclave the used casing before refilling it again with new fluid to be dispensed.

In an embodiment, the bottom part and the top part are integrally connected to one another by welding, particularly by ultrasonic welding. It has turned out that certain polymers or plastic materials are particularly appropriate for the bottom part and the top part since they allow for a fluid-tight welding with robustness also against temperatures at which autoclaving is usually performed. The bottom part and the top part of the casing may also be connected to one another by other fastening techniques such as screwing.

In an embodiment, the bottom part has a hollow stub (as an integral section of the bottom part) with a nozzle orifice at a top end. An internal volume of the stub may be coupled to the pressure feed unit. An external volume of the stub may be in fluid communication with the fluid accommodated in the casing. Therefore, the pressure feed unit being capable of providing a gas such as air under a high pressure of several bar or more may be conducted through an internal opening in the stub of the bottom part so as to bring it in interaction with the fluid.

In an embodiment, the casing has a hollow stub member (which may be a separate component to be assembled with the bottom part) with a further nozzle orifice at a top end, wherein the hollow stub member is to be mounted over the hollow stub for enclosing a (gap-like or tubular) fluid volume therebetween. The configuration may be so that upon feeding the internal volume of the stub of the bottom part with the pressurized medium to be ejected through its nozzle orifice, fluid is ejected through the further nozzle orifice. The hollow stub member may be also an injection molding piece. It can be configured with basically the same geometry but a slightly larger size as the stub of the bottom part. Therefore, a small hollow cylindrical void can be formed between the hollow stub and the hollow stub member, wherein fluid may enter this small gap, for instance as a result of capillary effects and other hydrostatic or hydrodynamic effects. Therefore, a proper interaction between the pressurized gas propagating through an interior of the hollow stub on the one hand and the fluid located around the hollow stub can be achieved.

In an embodiment, the top member has a deflecting member, particularly a deflecting pin, being configured so that, upon ejecting the fluid through the further nozzle orifice, the fluid is dispersed into the particles (particularly fluid particles) by an interaction with the deflecting member. The deflecting member may face a fluid emitting region of the nozzle orifice of the hollow stub member for a strong impact on fluid particle formation. Such a deflecting member may be arranged to face, with its fluid abutment surface, the nozzle orifice, thereby defining conditions of a collision between the disrupted particles (particularly fluid particles) on the one hand and the end face of the deflecting member on the other hand. The accelerated particles may therefore be suddenly decelerated by the deflecting member so that smallest particles can be generated.

In an embodiment, the top part has at least one predetermined breaking structure configured for being broken (i.e. destroyed irreversibly) by applying a breaking force so as to open (or to form) the fluidic path in the casing upon breaking. Such a predetermined breaking structure ("Sollbruchstelle") can be configured as a mechanically weakened portion of the top part which can be selectively destroyed for instance by a user using her or his muscle force so as to open the fluidic path (which may be formed by one or more fluid channels) in the top part of the casing.

Particularly, the breaking structure is configured for being broken irreversibly so as to exclude subsequent reclosure of the fluidic path. It may hence be mechanically excluded that the fluid cartridge is resealed or reclosed after first opening of the casing.

In an embodiment, the at least one predetermined breaking structure comprises at least one slanted plate located in an upper surface of the top part (and preferably protruding therefrom towards an exterior of the casing so as to be accessible for being broken by an externally applied breaking force) so as to be broken by bending or kinking the slanted plate(s) upon applying the breaking force. A slanted plate, i.e. a basically planar sheet protruding with an angle differing from 90° (for instance with an angle in a range between 60° and 85°) from a planar upper surface of the top part, is particularly suitable to be breakable with a small force in view of a relatively large lever arm formed by the slanted plate itself. This allows for an efficient transmission of a breaking force and therefore simplifies opening of the fluidic path by a user or a dispenser device.

In an embodiment, an anchoring of the at least one predetermined breaking structure in an upper surface of the top part is selectively mechanically weakened, particularly thinned, as compared to an environment of the upper surface. When the support of the breaking structure at a surface plate of the casing is selectively weakened locally by forming the material locally thinner, by using a less robust material at the anchoring and/or by perforating the anchoring, even a small breaking force may be sufficient to open the fluid cartridge for first use.

In an embodiment, the top part has at least one recess (particularly a plurality of circumferentially recesses) as the fluidic path, wherein the fluid cartridge further comprises a peelable layer being removable from the top part so as to expose the fluidic path. As an alternative to a breaking structure, it is therefore possible to provide a peelable layer (which may have a handle or grip or flap) allowing a user or the dispenser device to remove the peelable layer covering the recess(es), thereby exposing the recess(es) for providing fluid communication between an interior and an exterior of the cartridge. Therefore, before removing the peelable layer, the sterile configuration in the interior of the casing is maintained. The peelable layer may be sealingly connected to the casing by an adhesive material, by welding, by hot sealing, etc.

In an embodiment, the casing comprises a sealing member (such as a plug) forming at least part of the pressure feed interface and being penetrable by a pressure supply pin coupled to a pressure medium reservoir as the pressure feed unit. The sealing member may particularly be inserted into a through hole in a bottom surface of the bottom member. Therefore, a backside of the casing may have a sealing member which may be less stable or robust than the top and bottom parts of the casing (for instance may be made of another polymer material and/or may be made of thinner material). Upon pressing a pressure supply pin, which may have a sharp tip, through the sealing member, supply of pressurized medium such as a pressurized gas into an interior of the casing becomes possible.

Generally, the casing may comprise or consist of a thermoplastic and/or elastomeric material. Such a thermoplast and/or elastomer should be inert or basically inert with regard to an interaction with the fluid, particularly an active substance (such as a pharmaceutically active substance) thereof.

In order to further reduce such an interaction, coating of at least a part of the inner surface of the casing (contacting the fluid) may be appropriate so as to reliably decouple the fluid from the casing. Furthermore, such a material may reduce or eliminate undesired migration of material from the fluid into the casing. An example for a suitable coating is a coating with a fluoropolymer, particularly polytetrafluorethylene (PTFE). Such a coating may also suppress or eliminate leaching of substances (such as silicone, oil components, etc.) from the casing to the fluid, thereby keeping the fluid free of impurities. Additionally or alternatively to the coating, also adaptation of surface roughness of the inner surface of the casing is possible.

Generally, the casing may be made of a material or may be coated with a material which does not or basically does not interact with the fluid therein. The material should be selected so as to not have a negative impact on an active agent within the fluid.

In an embodiment, the casing comprises or consists of polyoximethylene (POM), also known as acetal, polyacetal, and polyformaldehyde. Extensive experiments of the present inventors have shown that POM is a particularly suitable casing material for the desired applications. On the one hand, POM is appropriate for being used for ultrasonic welding which is a highly advantageous connection technique for connecting top part and bottom part of the casing to one another. On the other hand, this material can also be autoclaved, i.e. is capable of withstanding the high temperatures in a range of for instance 90° C. to 140° C. applied during autoclaving. This is important for a sterile insertion of the fluid into the casing to be sealed later. For instance, autoclaving may involve heating the casing to 120° C. for 30 minutes.

In another embodiment, the casing comprises or consists of a copolymer of Acrylonitrile, Butodiene, and Styren, particularly Polylac ABS®. The chemical formula of such a material is $(C_3H_3N, C_4H_6, C_8H_8)_x$. Extensive experiments of the present inventors have shown that also Polylac ABS® is a highly appropriate material for the casing. This material has the specific advantage that it can be used for ultrasonic welding. The autoclaving properties are suitable for certain requirements. However, this material has the particularly advantage that it has a sufficient robustness for the fluidic particle formation process, which robustness is at the same time not too high so as to still enable breaking predetermined breaking structures with moderate force. Hence, it is particularly appropriate for forming slanted sheets or similar predetermined breaking structures used for fluidically opening the device by a user to get access to the fluid or liquid in it.

In an embodiment, the fluid cartridge itself comprises the pressure feed unit as a part thereof. In other words, the components housing the fluid including the provisions for the Venturi nozzle can be combined with the pressure feed unit (i.e. the source for the pressurized medium) for providing pressurized gas or the like in one single device. Particularly, fluid cartridge and pressure feed unit may together be configured as a portable device which can be handled manually by a user.

In an embodiment, the pressure feed unit comprises or consists of a pressurized medium accommodating container (such as a spray can or a gas bottle (particularly a nitrogen gas bottle, since nitrogen is biocompatible, cheap and a proper carrier gas for many therapeutic fluids such as hyaluronic acid)) accommodating the pressurized medium. The casing and/or the pressure feed unit has or have provisions so that the casing is mountable on the pressurized medium accommodating container (such as the spray can or the gas bottle) so that the pressure feed interface is supplyable with the pressurized medium from the pressurized medium accommodating container (such as the spray can or the gas bottle). In one embodiment in which the accommodated pressurized medium has a sufficient volume or mass, it is possible that the pressurized medium accommodating container (such as the spray can or the gas bottle) is usable for multiple fluid cartridges of fluid, whereas the casing with the fluid contained therein can be a disposable or single use component.

In an embodiment, the casing is detachably mountable on the pressure feed unit. In this embodiment, casing and pressure feed unit are two separable components so that for instance the casing can be exchanged by another casing when the fluid is empty but there is still pressurized medium left in the pressure feed unit.

In an alternative embodiment, the casing is integrally formed with the pressure feed unit. Both components may be formed as a single piece allowing for a compact arrangement. In this embodiment, the entire fluid cartridge can be formed of injection molding parts.

In an embodiment, the fluid cartridge or the arrangement comprises a respiratory mask connected to the fluidic path so as to guide the dispensed fluid towards a mouth and/or a nose of a user or an animal. In such an embodiment, it is possible that a tube or another fluidic particle transfer conduit can guide the generated fluidic particles (such as nanofluidic particles) towards a respiratory mask which a user wears on her or his face. Therefore, an efficient supply of the particles (particularly fluid particles) towards the nose or the mouth of the user and inside her or his body is possible.

In an embodiment, the fluid cartridge comprises a cartridge data carrier (such as a label attached to a surface of the fluid cartridge), particularly arranged at the casing, wherein the cartridge data carrier carries (for instance stores electronically in a memory such as a semiconductor memory) information assigned to the fluid cartridge. This information or data may be readable by a reader unit, particularly by a reader unit of the dispenser device. With such a cartridge data carrier it is possible to store data regarding the fluid cartridge, for instance indicative of a unique identification of a certain fluid cartridge. The cartridge data carrier containing or storing such an identifier may be integrally connected with the fluid cartridge. Therefore, it is possible for the dispenser device to unambiguously identify the fluid cartridge based on this information so as to render the whole dispensing procedure with this specific fluid cartridge reproducible and documentable. By taking this measure, it can also be ensured that each fluid cartridge is only used once and is for instance not misused by being refilled (for instance with a non-controllable substance, without sterile conditions, in a dangerous dosing, etc.). Therefore, the safety in use of the fluid dispenser system can be increased. Such an identifier of the fluid cartridge can be read out by the dispenser device upon accommodating the fluid cartridge in the fluid cartridge accommodation unit. Enablement of the fluid dispensing can be denied in case an identification reading process fails or yields the result that an identified fluid cartridge is not used for the first time, has been used a number of times exceeding a predefinable threshold value, or does not belong to an original manufacturer.

In an embodiment, the cartridge data carrier may be a transponder (particularly a radio frequency identification tag, RFID), a bar code (for instance a one dimensional bar code or a two dimensional bar code, wherein such a bar code may be read out optically), and a holographic foil (wherein information stored in a corresponding hologram may be read out optically). All these examples for appropriate cartridge data carriers which for instance may be adhered to an external or an internal surface of the casing may all carry or store the required information.

In an embodiment, the cartridge data carrier carries cartridge identification information being uniquely indicative of an identity of the fluid cartridge, and/or indicating a date of expiry until which the fluid cartridge is usable (i.e. a "best before" date), and/or may include (or may include a link to) operation data indicative of an operation mode according to which the fluid cartridge is usable by a dispenser device. For instance, when the reading of the cartridge identification information shows that the same fluid cartridge has already been used in the past, further use may be inhibited by the dispenser device. Such data may also be received by the dispenser device over a communication network such as the public Internet. If the date of use is later than the date of expiry, use of the fluid cartridge may be denied. It is also possible that the way of operating the fluid cartridge for a certain dispensing procedure is determined based on certain data. The dispenser device may then read a set of operating parameters for fluidic particle formation from the cartridge data carrier (for instance may determine which kind of pressure, which kind of metering, etc. is suitable for the particular fluid of the fluid cartridge).

In an embodiment, the cartridge data carrier is configured so as to enable a data writing unit, particularly a writing unit of the dispenser device, to write data onto the cartridge data carrier (for instance to write electronic data into a cartridge data memory). In such an embodiment it is possible that the fluid dispensing history is documented directly in the cartridge data carrier of the fluid cartridge (for instance a flag may be set indicating that this specific fluid cartridge has already been used once).

Such a cartridge data carrier may be a physical data carrier (encoding the stored information via physical structures such as alternating sequence of light and dark bars) or an electronic data carrier (storing the information in a volatile or non-volatile memory such as an EEPROM). It may be exchanged and accessed in a wired or in a wireless manner. For a wireless communication, the cartridge data carrier may have a transmission and/or receiver coil.

In an embodiment, the fluid cartridge is configured so that a dimension of at least about 50%, particularly of at least about 80%, more particularly of at least about 95%, of the dispensed particles (such as dispensed fluid particles) is in a range between about 10 nm and about 1000 nm, particularly is in a range between about 60 nm and about 200 nm. The smaller the particles, the deeper will the particles penetrate into a body of a human being or an animal. A too deep penetration into the body may involve a medical risk (such as pulmonary embolism). However, if the particles become too large, their influence on the physiological subject (such as the human being or the animal) becomes too small. The given ranges are a reasonable tradeoff between these two boundary conditions.

The dispensed particles may lose at least a part of their liquid constituents (and/or of their gaseous constituents) after their generation by evaporation or the like. In case they lose a part of their liquid and/or gaseous constituents, they remain fluid particles. In an extreme case, the dispensed particles lose basically all of their liquid and/or gaseous constituents. The dispensed particles may be, directly after their generation, dispensed fluid particles. During propagation along their propagation path, they may be converted from dispended fluid particles into dispended particles without liquid and gas, i.e. into solid particles.

In an embodiment, the casing accommodates the fluid. For instance, the amount of accommodated fluid may be in a range between 1 ml and 50 ml, particularly may be in a range between 3 ml and 10 ml. Such dimensions are suitable for medical and wellness applications. However, in order to perform disinfecting operations or the like, the amount of accommodated fluid may be in a range between 50 ml and 10 l, particularly may be in a range between 1 l and 5 l.

The fluid may comprises for instance hyaluronic acid—also called hyaluronan or hyaluronate—(preferably a mixture of hyaluronic acid and sodium chloride solution), olive oil, an essential oil, dead sea salt, dead sea salt with L-ascorbate, evening primpose oil, black cumin oil, aloe vera, algae extract, cucumber, avocado oil, D-panthenol an oil-coated active agent, a human medication, a veterinary medication, a wellness preparation, citric acid, and/or ozone. However, these fluids or liquids are only examples, and any other kind of physiologically active fluids may be implemented for the treatment of human beings or animals for the purpose of wellness or medical treatment or for other purposes such as disinfection. An oil-coated active agent has the advantage that the oil coating is removed within a physiological body (such as a human or an animal) with a certain delay, resulting in a delayed release of the active agent (such as a pharmaceutical agent). Aloe vera has an anti-inflammatory effect and has an anti-aging effect. Alga extracts are antimicrobial, and have an anti-aging effect on lungs and skin and tighten/lift the skin. Cucumber has an anti-aging effect and tightens/lifts the skin. D-panthenol promotes formation of new cells. Panthenol is the alcohol analog of pantothenic acid (vitamin $B_5$), and is thus a provitamin of $B_5$. All these material are eye-compatible and harmless to ocular tissues. Particularly preferably is a mixture of hyaluronic acid and sodium chloride solution with a hyaluronic acid concentration in a range between 0.1 weight % and 2 weight %, particularly between 0.5 weight % and 1 weight %. With lower concentrations, the effect may become too weak. With higher concentrations, the solution may become too viscous for the proper formation of nanofluidic particles.

In an embodiment, the casing accommodates a solid precursor, particularly a powder or a granulate, of the fluid, wherein the solid precursor is mixable with a liquid, particularly with water, to thereby form the fluid in the casing. Hence, the container may be filled with a powder or a granulate or any other kind of suitable solid material. Only short before use, a liquid such as water can be added to the solid to form the fluid (which may be a liquid or a suspension). Therefore, the date of expiry of the fluid cartridge can be extended since the material to be dispensed is dry and is only rendered fluidic directly before use.

The liquid to be mixed with the solid precursor may be arranged in an aseptic condition within the casing in a compartment being separate from another compartment within the casing in which the solid precursor is located. Before use, the compartments may be brought in fluid communication with one another, for instance by removing a separating wall between the compartments. Alternatively, it is also possible to accommodate only the solid precursor within the casing and to supply the liquid to the fluid cartridge, for instance directly before use of the fluid cartridge for dispensing fluid, via a sealed and sterile fluid interface of the fluid cartridge (i.e. in a similar way as the pressurized medium is supplied to the interior of the casing).

In the following, further exemplary embodiments of the dispension device will be explained. However, these embodiments also apply to the fluid cartridge, the method of operating a fluid cartridge, the method of operating a dispension device, the arrangement, and the method of use.

In an embodiment, the dispenser device comprises a fluid cartridge opening mechanism configured for opening a fluidic path via which the particles (particularly fluid particles) leave the casing upon accommodating the fluid cartridge in the accommodation unit. For instance, the opening mechanism may operate by breaking at least one predetermined breaking structure of the fluid cartridge by applying a breaking force. Therefore, the dispenser device itself may have a mechanism for opening the fluid cartridge so that a user does not have to fulfil this task manually. For instance, when inserting the fluid cartridge in the dispenser device, the mechanism may be activated (for instance when a user presses a certain button or pivots a certain lever) to break a part of the casing so as to enable access to the opening.

In an embodiment, the dispenser device, particularly the cartridge accommodation unit, comprises a read and/or write unit (such as an RFID read/write device or an optical bar code scanner) configured for reading data from and/or writing data to a cartridge data carrier of the fluid cartridge upon accommodating the fluid cartridge at the cartridge accommodation unit. Thus, data exchange between dispenser device and fluid cartridge can be performed in a unidirectional or bidirectional way.

In an embodiment, the dispenser device further comprising a further cartridge accommodation unit configured for accommodating a further fluid cartridge having a further fluid in a further casing, and a further pressure feed mechanism configured for feeding the further fluid in the further casing with a further pressure upon accommodating the further fluid cartridge in the further accommodation unit to thereby generate further particles (particularly fluid particles) leaving the further casing upon feeding the further fluid in the casing with the pressure. Therefore, it is possible to have two or more different fluid cartridges used at the same time. With such a provision, a co-medication can be performed supplying a mixture of multiple active agents at the same time. In case of multiple cartridges, each cartridge may be supplied individually with a separate pressurized medium via a pressure feed mechanism assigned only to the respective fluid cartridge. Alternatively, different fluid cartridges may be served by one and the same pressure feed mechanism. In other words, the pressure feed mechanism and the further pressure feed mechanism may be combined to a single pressure feed mechanism.

In another embodiment, it is however also possible to have exactly one fluid cartridge inserted into the dispenser device at a time.

In an embodiment, the dispenser device comprises a control unit configured for controlling operation of the pressure feed mechanism and of the further pressure feed mechanism to thereby adjust a dispensed composition between particles (particularly fluid particles) and the further particles (particularly fluid particles). Such a control unit may be a processor such as a microprocessor or a central processing unit (CPU) and may define a mode of supplying two or more different fluids simultaneously so as to precisely define relative amounts of dispensed fluids, a timing, etc.

In an embodiment, the cartridge accommodation unit comprises a fluid cartridge receptacle, particularly provided as a separate body, for receiving a section (for instance an upper section) of the fluid cartridge and having an engagement element (for instance a groove to be engaged or a protrusion for engaging). A mounting support may have a complementary engagement element (for instance a protrusion for engaging or a groove to be engaged) for engaging or for being engaged by the engagement element for holding the fluid cartridge receptacle receiving the fluid cartridge. For instance, an upper portion of the fluid cartridge may be inserted in the cartridge accommodation unit, whereas the lower part thereof may remain exposed to the environment and may therefore protrude over the fluid cartridge receptacle. Then, the engagement element of the cartridge accommodation unit may be fastened at the engagement element of the mounting support such as a mounting plate. The fluid cartridge together with the fluid cartridge receptacle (which may be made of a metal such as stainless steel) are fixed at a certain position at the mounting support.

In an embodiment, the fluid cartridge receptacle has a through hole for exposing an opened fluid conduit of the fluid cartridge to an environment when the fluid cartridge receptacle receives the fluid cartridge. The through-hole may allow the dispensed fluid to be emitted towards the environment.

In an embodiment, the pressure feed mechanism comprises a pressure supply pin (such as a tubular body with a sharp tip) coupled to a pressure medium reservoir (which may accommodate the pressurized medium). The pressure supply pin may be configured for penetrating a surface of the fluid cartridge (for instance a sealing plug in a bottom surface thereof) for feeding the fluid in a casing of the fluid cartridge with a pressure. A drive unit of the pressure feed mechanism may be configured for driving the pressure supply pin into the surface of the fluid cartridge mechanism. In such an embodiment, it is possible to automatically trigger pressure supply to the fluid filled casing by a drive unit such as a motor. Therefore, impact of muscle force of a user is not necessary in such an embodiment.

In an embodiment, the drive unit is configured for driving, particularly for raising, a movable force transmission plate towards the static mounting support (at which the fluid cartridge is mounted, for instance via a fluid cartridge receptacle) to thereby drive the pressure supply pin through the surface of the fluid cartridge in fluid communication with the interior volume of the casing. In this embodiment, the fluid cartridge received in the fluid cartridge receptacle, the latter being in turn received by the mounting support, can be supplied with pressurized gas by moving the movable force transmission plate towards the static mounting support until a sharp pin penetrates the casing from a backward side. This renders operation of the dispenser device user friendly.

In an embodiment, the drive unit comprises a motor for providing a driving force to the force transmission plate and comprises a guide mechanism for guiding the force transmission plate towards the mounting support along a predefined trajectory (for instance so that the force transmission plate and the mounting support are always parallel to one another which may be advantageous particularly when multiple fluid cartridges are handled at the same time). The motor provides the driving force, whereas the guide mechanism allows for a parallel motion between force transmission plate and mounting support plate.

In an embodiment, the drive unit is a linear motor. The guide mechanism may comprise a guide bearing cooperating with a knee lever, i.e. pivotable legs convertible between a straight and an angled configuration and being mechanically coupled to the force transmission plate which is turn guided by the guide bearing. Therefore, the linear motor provides for a linear motion, which bends the knee lever so that the force transmission plate is moved in a guided manner along the guide bearing.

In an alternative embodiment, the pressure feed mechanism comprises a pressure supply pin coupled to a pressure medium reservoir and being configured for penetrating a surface of the fluid cartridge for feeding the fluid in a casing of the fluid cartridge with a pressure. Additionally, a lever mechanism actuable by a user may be provided, wherein the pressure supply pin penetrates the surface of the fluid cartridge upon actuating (for instance pivoting) the lever mechanism. In this alternative embodiment, muscle force of a user who actuates a lever is used to initiate the supply of pressurized gas to the interior of the casing.

In an embodiment, the pressure feed unit is configured for supplying the pressurized medium with a pressure in a range between about 1,1 bar (i.e. slightly above atmospheric pressure) and about 10 bar, particularly about 1,5 bar and about 10 bar, more particularly in a range between about 2 bar and about 5 bar. In this pressure range, generation of fluidic particles in the nanofluidic range is possible.

In an alternative embodiment, the pressure feed unit is configured for supplying the pressurized medium with a pressure in a range between about 50 bar and about 1000 bar, particularly in a range between about 200 bar and 600 bar. In this pressure range, generation of fluidic particles with a highly advantageous impact on cells and there activation is possible. Without wishing to be bound to a specific theory, it is presently believed that such pressure values are capable of generating so-called "biophontons", i.e. energy propagating into the body of the physiological subject. Adjustment of the dimension of the generated fluidic particles can be done by adjusting the size of the orifice(s) of the nozzle. The given high pressure values are obtained by selecting a sufficiently small nozzle size.

In an embodiment, the pressure feed unit comprises a plurality of separate pressurized medium chambers each configured for supplying a respective pressurized medium to the fluid in the casing of the fluid cartridge to thereby generate the particles (particularly fluid particles) leaving the casing. In other words, it is possible that different gas chambers (which may be filled with different pressurized kinds of gas) are provided. One or more of the pressurized medium chambers may be selected at a time for supplying gas to the fluid cartridge.

In an embodiment, the dispenser device comprises a temperature adjustment unit, particularly a heating unit and/or cooling unit, configured for adjusting a temperature of the pressurized medium in the pressure feed unit. For instance, a Peltier element integrated in one or more of one or more pressurized medium chambers may allow to adjust the temperature of the respective pressurized medium to a desired value. Adjusting the temperature may include heating to an elevated temperature or cooling to a lower temperature (for instance as compared to ambient temperature).

In an embodiment, the dispenser device comprises a control or regulating unit configured for controlling and/or regulating which of the plurality of separate pressurized medium chambers supplies its respective pressurized medium to the fluid in the casing and/or configured for controlling and/or regulating the temperature of the pressurized medium in the pressure feed unit. Such a control unit may control, for instance based on a stored algorithm or in accordance with a user input, which of pressurized medium chambers is activated for transporting its gas to the casing. Such a control unit may control, for instance based on a stored algorithm or in accordance with a user input, to which temperature a pressurized medium is to be heated or cooled. A regulating unit may regulate, based on a feedback signal including a regulation information (such as a filling level or a temperature of one or more pressurized medium chambers), which of the pressurized medium chambers is activated and/or to which temperature pressurized medium in a pressurized medium chamber is to be heated or cooled.

In the following, further exemplary embodiments of the arrangement will be explained. However, these embodiments also apply to the fluid cartridge, the dispension device, the method of operating a fluid cartridge, the method of operating a dispension device, and the method of use.

In an embodiment, the fluid cartridge comprises a tamper-proof feature being indicative of an origin of the fluid cartridge. The dispenser device may be equipped with a corresponding tamper-proof verification unit configured for verifying whether a fluid cartridge accommodated by the dispenser device has a tamper-proof feature being indicative of an approved origin of the fluid cartridge. The dispenser device may enable generation of particles (particularly fluid particles) only upon verification that the fluid cartridge has the tamper-proof feature. The dispenser device may disable generation of particles (particularly fluid particles) when the verification that the fluid cartridge has the tamper-proof feature fails. Such a tamper-proof feature may be a tamper-proof indicia or marker which is detectable or readable by the dispenser device. The tamper-proof indicia or marker can be data (such as an alphanumerical code, a two- or three-dimensional bar code, electronic data stored in a memory of a transponder), a color, a hologram, a mechanical surface structure, etc.

In an embodiment, the fluid cartridge and/or the dispenser device may be configured so that the tamper-proof feature is irreversibly destroyed or deactivated upon first insertion of the fluid cartridge into the dispenser device. For instance, a predetermined breaking point of the fluid cartridge may break during the first insertion, identification data may be erased from a memory of the fluid cartridge, deactivation data may be stored in a memory of the fluid cartridge, etc. Hence, it can be ensured that a once used fluid cartridge is used again, thereby increasing safety of operation and avoiding damage to health of a user.

The arrangement may comprise a particle source and a respiratory mask fluidically connected to the particle source so as to guide further fluidic particles towards a mouth and/or a nose of a physiological subject, particularly a human being or an animal, via the respiratory mask. The particle source may be provided separately from the fluid cartridge and the dispenser device. Hence, the skin of a user may be treated with the particles (particularly fluid particles) leaving the casing of the cartridge, while other fluidic particles from the particle source may allow a treatment of the respiratory tract of the user. In one embodiment, the particle source may comprise a fluid cartridge and a dispenser device having the above-described features.

In the following, further exemplary embodiments of the method of use will be explained. However, these embodiments also apply to the fluid cartridge, the dispension device, the method of operating a fluid cartridge, the method of operating a dispension device, and the arrangement.

In an embodiment, the arrangement is configured as a closable (particularly via a door) treatment cabin dimensioned so that a human being, as the physiological subject, is treated with the particles (particularly fluid particles) within the closed cabin. Such an arrangement may have a closable door via which the human being may enter the treatment cabin. Within the treatment cabin, the human being may take a seat before the fluid is sprayed from the fluid cartridge into an interior space of the cabin.

Optionally, such a cabin may be equipped with a separate oxygen supply line (for instance connected to a respiratory mask) for supplying oxygen into the cabin. For example, a user may wear a respiratory mask supplied with an extra amount of oxygen during the treatment. This may be particularly appropriate for medical applications and may avoid lack of sufficient oxygen during a treatment involving a non-inhalable fluid.

In an embodiment, the arrangement is configured as a closable treatment cabin dimensioned so that an animal, particularly a bird (such as a falcon) or a horse, can be treated as the physiological subject with the particles (particularly fluid particles) within the closed cabin. However, as an alternative, other animals may be treated as well in such a cabin.

It is possible that cabins of different sized are provided such as one dimensioned for birds, another one dimensioned for small animals such as cats or dogs, and a further one dimensioned for l In an embodiment, the arrangement is configured as a portable device dimensioned so that a human being, as the physiological subject, is treated with the particles (particularly fluid particles) by manually handling the device. Therefore, the arrangement may be configured so that it can be carried by a user during normal use. For example, the portable or handheld device may be storable within a pocket. If a user wishes a treatment, she or he simply activated the generation of fluidic particles by the device in a for instance closed room.

Such a portable device, for instance configured as a combination of an aerosol can and a selectable cartridge, can be used as a user-specific device for everyday use. By selecting a cartridge or a combination of cartridges to be used for the portable device, a user can for instance define a specific vitamin composition or other composition to be inhaled.

In an embodiment, the arrangement is configured to be installed in a room so as to treat a human being, as the physiological subject, present in the room with the particles (particularly fluid particles). For example, such an arrangement may be a sauna or an office room in which a person is brought in contact with the atomized particles (or aerosol) ejected from an apparatus.

In an embodiment, the arrangement is used for disinfecting a room (such as a room in a hospital, or the interior of a car). For example, cartridges with a fluid accommodation volume (dimension) of at least about 1 l, particularly in a range between about 1 l and about 10 l can be used for such a purpose. Ozone, citric acid or other disinfecting materials may be used for such a purpose as the fluid.

The aspects defined above and further aspects of the invention are apparent from the examples of embodiment to be described hereinafter and are explained with reference to these examples of embodiment.

The invention will be described in more detail hereinafter with reference to examples of embodiment but to which the invention is not limited.

The illustrations in the drawings are schematical. In different drawings, similar or identical elements are provided with the same reference signs.

FIG. 1 illustrates an arrangement 180 for dispensing a liquid such as hyaluronic acid into nanofluidic particles according to an exemplary embodiment of the invention.

The arrangement 180 comprises a disposable liquid cartridge 100 in which the liquid 192 is accommodated. For instance, 4 ml of the liquid 192 are filled in the fluid cartridge 100 which has been packaged in a sterile way.

Figure 1:
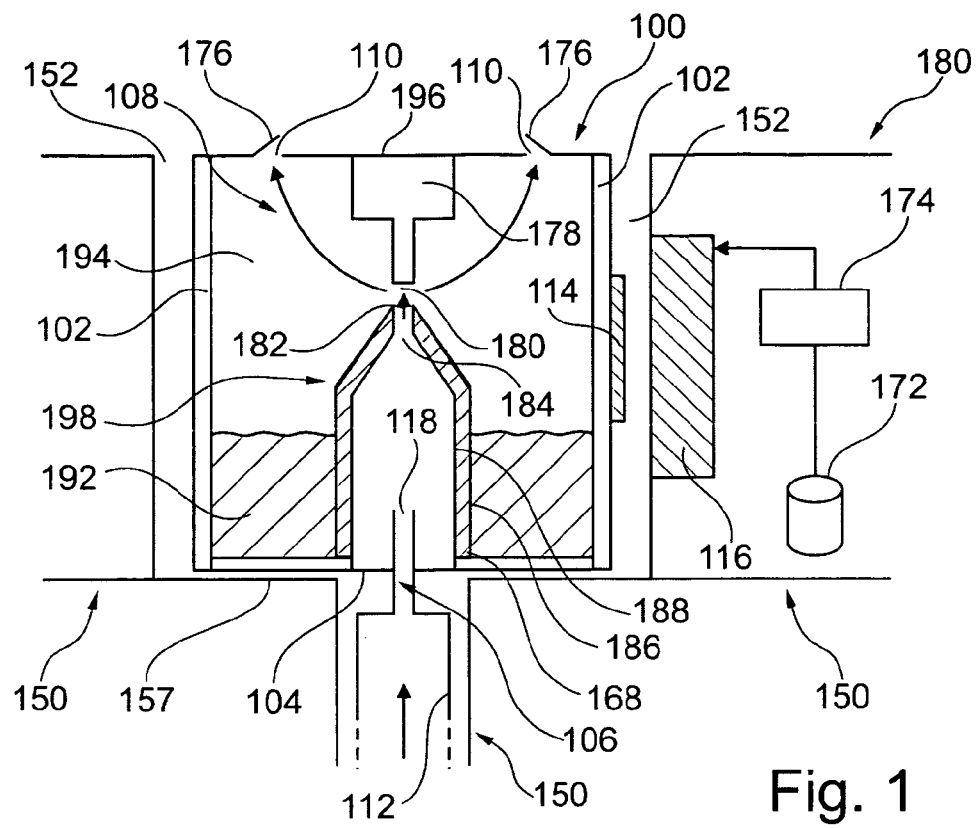
FIG. 1 illustrates an arrangement of a dispenser device and a fluid cartridge according to an exemplary embodiment of the invention.

The liquid cartridge 100 is, in the configuration of FIG. 1, already accommodated in a dispenser device 150 for dispensing the liquid from the liquid cartridge 100. In other words, nanoparticles of the liquid are to be sprayed into a room surrounding arrangement 180 so that a user can inhale the particles for wellness or medical purpose.

The liquid cartridge 100 is configured for dispensing the liquid 192 and comprises a hermetically sealed housing or casing 102 within which the liquid 192 is accommodated. A pressure feed interface 104 is foreseen at a bottom of the hermetically sealed liquid cartridge 100 and is configured for being fluidically coupled to a pressure feed unit 106 of the dispenser device 150. Pressure feed unit 106 of the dispenser device 150 is configured for supplying the liquid 192 in the casing 102 with pressurized air. In other words, pressure feed unit 106 is fluidically coupled or in fluid communication with the pressurized gas to be supplied.

Furthermore, as will be explained below in more detail, the liquid cartridge 100 comprises a liquid dispensing portion 108 which is configured for generating the nanofluidic liquid particles within hollow chamber 194 delimited by the casing 102 upon providing the liquid 192 in the casing 102 with the pressurized gas. Several fluid channels 110 are circumferentially arranged in a top plate 196 of the casing 102. The fluidic channels 110 can be selectively opened for enabling the liquid particles to leave the casing 102 through the fluidic channels 110. Thereby, it is possible to generate the dispensed or atomized liquid in the form of nanoparticles.

Within the casing 102, a Venturi nozzle 198 is provided which is composed exclusively by injection molding parts, thereby allowing to manufacture the liquid cartridge 100 with low cost. The Venturi nozzle 198 consists of two stub-like elements 188, 186 each shaped as a hollow cylinder with a cone-like tip. Note that stub-like element 188 sealingly contacts bottom surface 157 of the casing 102, whereas a lower end of stub-like element 186 is spaced with regard to bottom surface 157 of the casing 102 by a small gap 168 allowing liquid 192 to flow between stub-like elements 188, 186. In an interior of inner stub 188 the pressurized air can flow in an upward direction. Without wishing to be bound to a specific theory, it is presently believed that liquid 192 is present in the small gap between the stubs 186, 188. When the pressurized air propagates in an upward direction according to FIG. 1, liquid particles are disrupted from the liquid surface in the gap between stubs 186, 188 and will be moved upwardly. Orifices 184, 182 of the stubs 186, 188 will focus the liquid particles onto an opposing surface 180 of a deflecting element 178, thereby generating nanoparticles. Relatively heavy liquid particles will be forced downward under the influence of gravitation so that they will be reunified with the liquid 192. However, the very small and light nanoparticles specifically with a size between 60 nm and 200 nm will be moved upwardly and will leave the hollow chamber 194 within the casing 102 through the fluidic channels 110. Therefore, externally of the casing 102, an atomized atmosphere of the liquid material will be present which can then be inhaled by the user.

The fluidic channels 110 can be formed in the casing 102 using predetermined breaking structures 176 which are already destroyed in the illustration of FIG. 1. Before the liquid cartridge 100 is in first use, the predetermined breaking structures 176 are still intact and hermetically seal upper surface 196 of the casing 102. However, these predetermined breaking structures 176 can be selectively broken by a user since they are configured as mechanically weakened portions of the top surface of the casing 102. Breaking the predetermined breaking structures 176 will enable or start the nanoparticle formation. Irreversible breakage of the predetermined breaking structures 176 renders the liquid cartridge 100 incapable of being used again because sterility is lost. Therefore, the provision of the predetermined breaking structures 176 can be considered as a safety feature to ensure that the liquid 192 is in fact sterile before a first use.

The casing 102 is also sealed in a bottom portion before the pressure feed unit 106 penetrates the casing 102. The pressure feed interface 104 can be for instance a membrane or a less robust plastic material as compared to the rest of the casing 102, so as to enable a sharp pressure feed pin 118 to penetrate the pressure feed interface 104 to thereby allow it to provide pressurized gas to an interior of the casing 102.

FIG. 1 furthermore shows that the liquid cartridge 100 has an adhering label in the form of a cartridge data carrier 114 attached to an outer surface of the liquid cartridge 100. The cartridge data carrier 114 carries or stores information assigned uniquely and individually to the liquid cartridge 100. This information or data can be read out by a reader unit 116 of the dispenser device 150. The cartridge data carrier 114 is an RFID tag which can be made subject of a reading or writing operation by the reader/writer unit 116 of the dispenser device 150. For instance, information unambiguously indicative of an identity of the liquid cartridge 100 can be stored on the cartridge data carrier 114, for instance in form of an alphanumerical code. This information can be read out by the reader/writer unit 116 of the dispenser device 150 in a wireless manner as known by those skilled in the art. Additionally or alternatively to the identification of the liquid cartridge 100 (making misuse, for instance in form of non-certified cartridges, less probable) it is also possible that other kind of information is stored in a semiconductor memory of the RFID tag 114. For instance, a date of expiry after which the liquid 192 within the casing 102 should no more be used can be stored on the RFID tag 114 and may be read out and verified by reader 116 before enabling liquid dispensing, otherwise liquid dispensing may be refused by dispenser device 150. Furthermore, operation information (such as one or more parameter values of a dispensing procedure) according to which the liquid cartridge 100 should be operated by dispenser device 150 can be stored on the RFID tag 114 and may be read out by reader 116 as a basis for a subsequent control of the corresponding dispensing procedure.

Also, it is possible that the read/write unit 116 of the dispenser device 150 writes data in the memory of the cartridge data carrier 114 of the liquid cartridge 100, for instance to document the history of the use of the liquid cartridge 100. Such a documentation is highly advantageous in the field of medical devices because it allows later to retrace unambiguously which history the liquid cartridge 100 has been subjected to.

Referring now to the dispenser device 150, it should first be said that it comprises a cartridge accommodation unit 152 in the form of a suitable receptacle configured to receive liquid cartridge 100 and to fasten it at a predefined position. Furthermore, the pressure feed unit 106 is part of the dispenser device 150 and is configured for providing the liquid 192 in the casing 102 of the liquid cartridge 100 with pressurized gas upon accommodating the liquid cartridge 100 in the cartridge accommodation unit 152. As discussed above, it is thereby possible to generate liquid particles which leave the casing 102 upon supplying the gas pressure to the liquid 192 in the casing 102.

Furthermore, the read/write unit 116 being capable for reading information from RFID tag 114 and writing information into the RFID tag 116 is provided and comprises components such as coils, processing circuitry, etc. The spatial range over which the read/write unit 116 may communicate with the RFID tag 114 can be adjusted so that only liquid cartridges 100 being inserted into the accommodation space 152 can be read out so as to avoid undesired read and write operations. Furthermore, the read/write unit 116 can be controlled by a control unit 174 of the dispenser device 150. Control unit 174 is capable of exchanging information with a database 172 in which for instance operation parameters for operating different kinds of liquid cartridges 100 can be stored.

Figure 2:
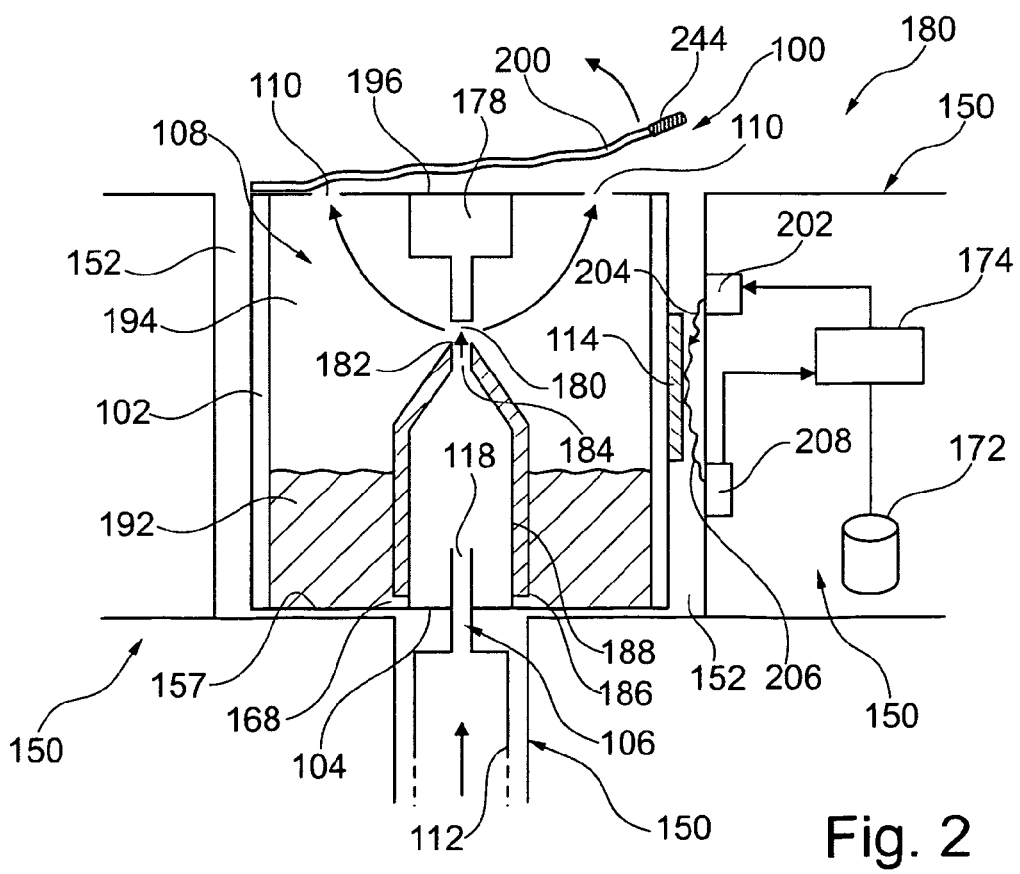
FIG. 2 illustrates an arrangement of a dispenser device and a fluid cartridge according to another exemplary embodiment of the invention.

FIG. 2 shows an arrangement 180 according to an exemplary embodiment which is also constituted by a liquid dispenser 100 and a corresponding dispenser device 150. In contrast to the embodiment of FIG. 1, the embodiment of FIG. 2 does not have predetermined breaking structures 176, but in contrast to this a peelable liquid-tight plastic layer 200 adhering on upper surface 196 of the casing 102. As indicated by an arrow in FIG. 2, a user may grip a flap 244 of the peelable layer 200 so as to remove it from the upper surface 196 of the casing 102, thereby exposing the fluidic channels 110 arranged circumferentially on top of the casing 102.

A second difference between the embodiment of FIG. 1 and the embodiment of FIG. 2 is that in the embodiment of FIG. 2, the cartridge data carrier 114 is a holographic foil which can be read out by an optical readout system. This optical readout system comprises a light source 202 capable of irradiating a light beam 204 onto the holographic foil 114. After interaction with (particularly reflection on) the surface of the holographic foil as cartridge data carrier 114, the reflected light beam 206 (having properties being dependent on the information stored on the holographic foil) can be detected by a photodetector 208 such as a photodiode. Control unit 174 is capable of deriving the data stored or encoded in the cartridge data carrier 114 based on the signal detected by photodetector 208 so as to identify the liquid cartridge 100, etc.

In the following, referring to FIG. 3 to FIG. 9 a liquid cartridge 100 according to an exemplary embodiment of the invention will be explained which is formed of four different injection molding parts.

Figure 3:
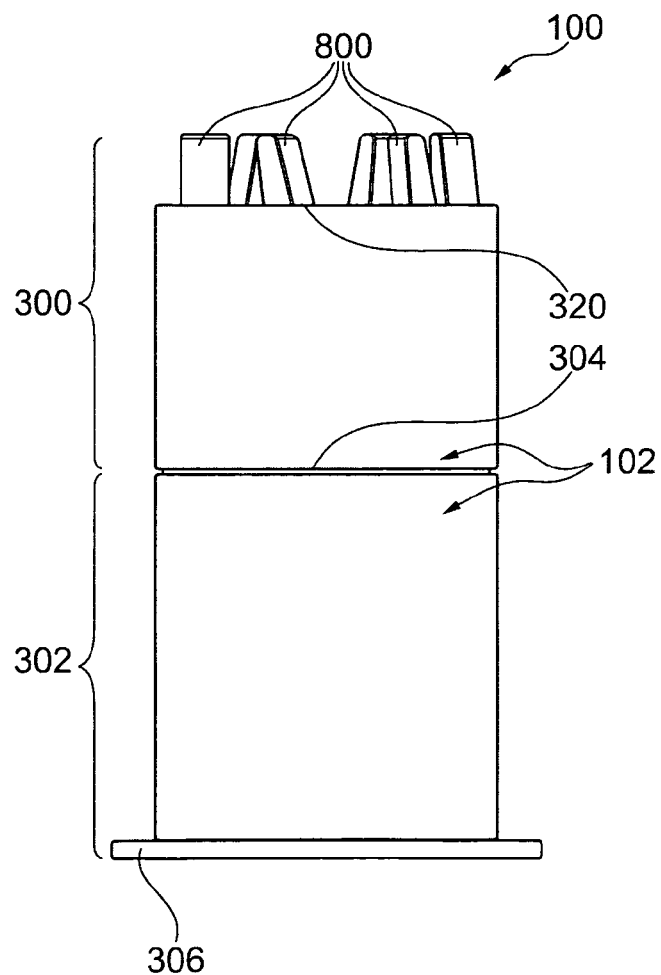
FIG. 3 shows a fluid cartridge according to an exemplary embodiment of the invention in a sealed state.

As can be taken from FIG. 3, the casing 102 shown there has a bottom part 302 and a top part 300. The bottom part 302 and the top part 300 are integrally connected to one another in a hermetically sealed fluid-tight manner and in a sterile manner. Particularly, an ultra-welding seam 304 connects the top part 300 with the bottom part 302. Slanted plates 800 are provided on a top plate 320 of the upper part 300 and are arranged circumferentially thereon. Breaking the slanted plates 800 will allow to produce fluidic channels in the top plate 320 of the top part 300 thereby enabling fluid communication between an interior and exterior of the casing 102. As can further be taken from FIG. 3, the mounted state of casing 3 is a basically cylindrical structure with a circular bottom plate 306.

Figure 4:
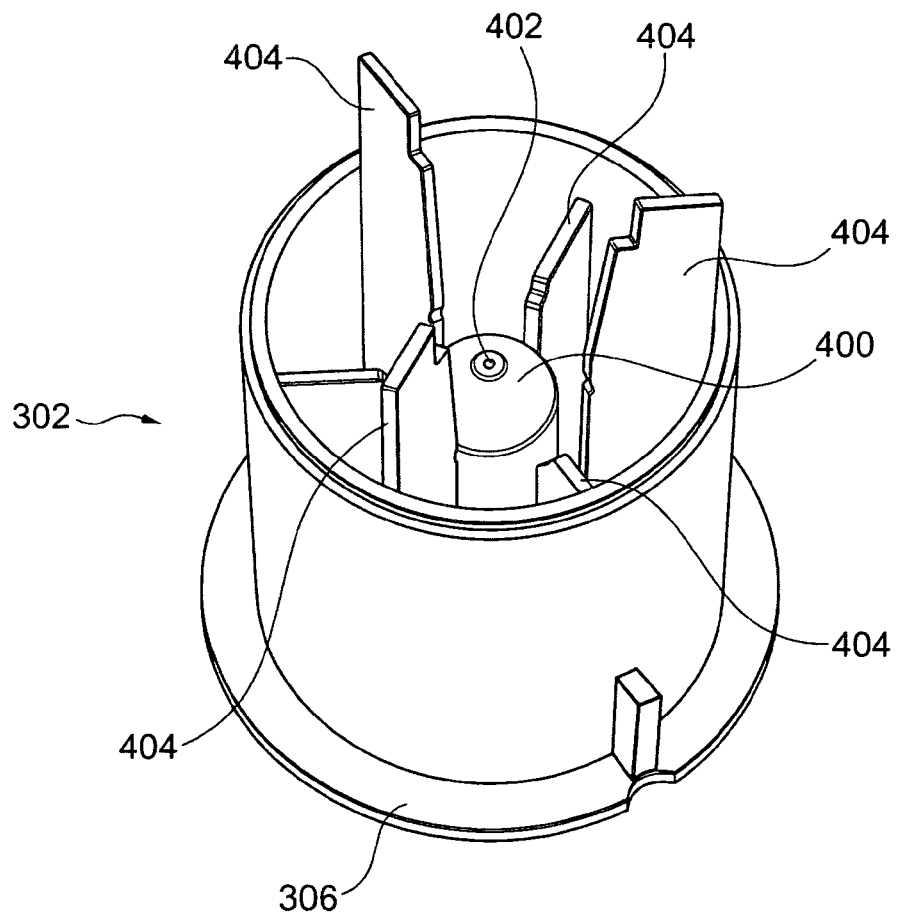
FIG. 4 shows a bottom part of the fluid cartridge of FIG. 3.
Figure 5:
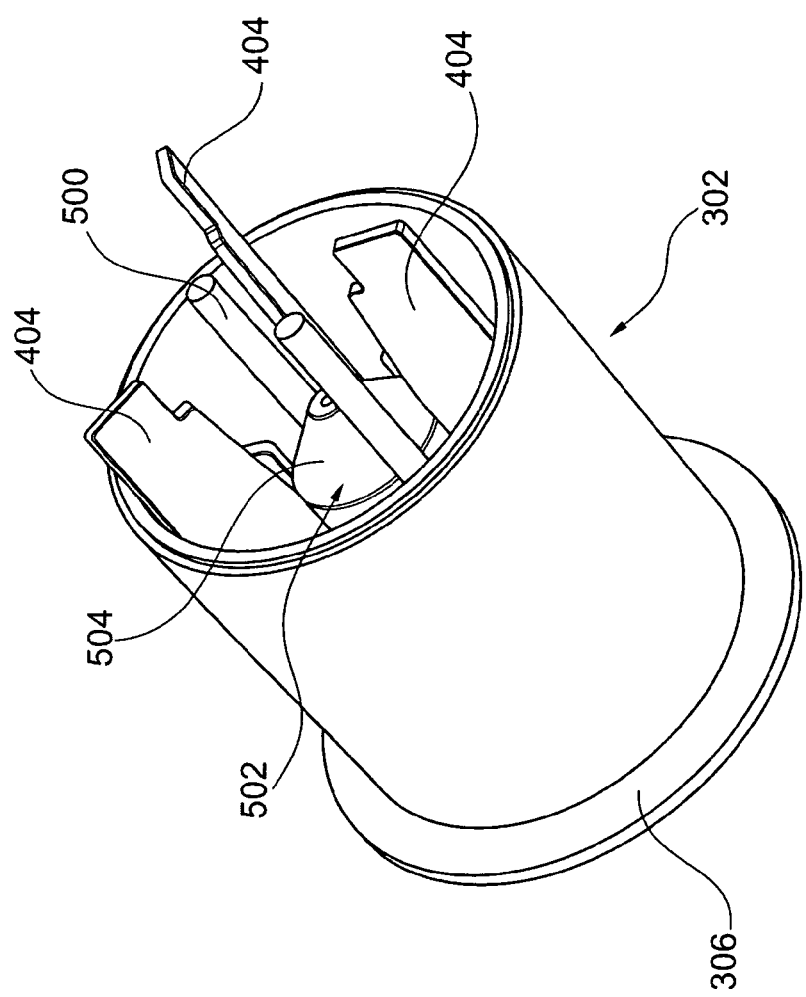
FIG. 5 shows the bottom part of the cartridge of FIG. 3 with an inserted separate hollow stub member.

FIG. 4 shows the bottom part 302 without the top part 300 and indicates that the bottom part 302 has a hollow stub 400 with a nozzle orifice 402 at a top end thereof. An internal volume of the bottom part 302 will accommodate the liquid. An internal volume of the stub 400 can be coupled to a pressure feed unit 106, and an external volume of the stub 400 within the casing 102 can be in fluid communication with the liquid accommodated in the casing 102. FIG. 4 furthermore shows an arrangement of blades 404 dividing the internal volume within the bottom part 302 into several compartments and stabilizing the entire structure.

FIG. 5 again shows the bottom part 302, wherein a hollow stub member 502 being a separate injection molding part has been slid over stub 400 to cover the latter. Hollow stub member 502 has a further nozzle orifice 504 at a top end, wherein the hollow stub member 502 is mounted over the hollow stub 400 for enclosing a liquid volume therebetween so that, upon feeding the internal volume of the stub 400 with the pressurized air to be ejected through the nozzle orifice 402, liquid is ejected through the further nozzle orifice 504. This mechanism has been described above referring to FIG. 1.

Figure 6:
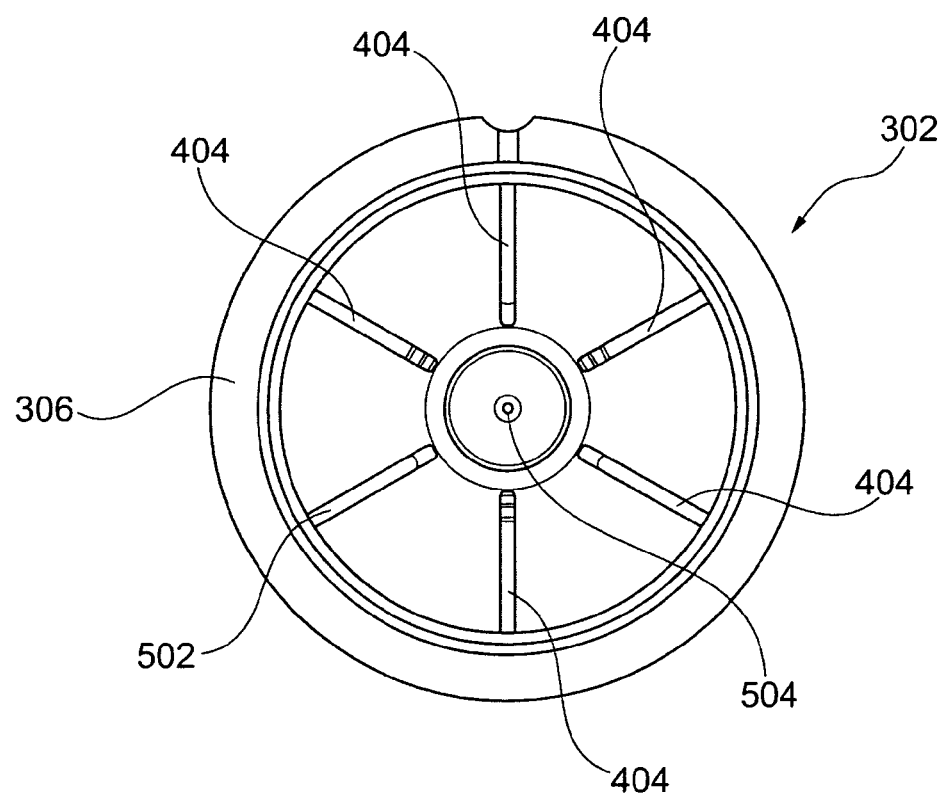
FIG. 6 shows a plan view of the arrangement of FIG. 5.

FIG. 6 shows a plan view of the bottom part 302 with the attached hollow stub member 502.

Figure 7:
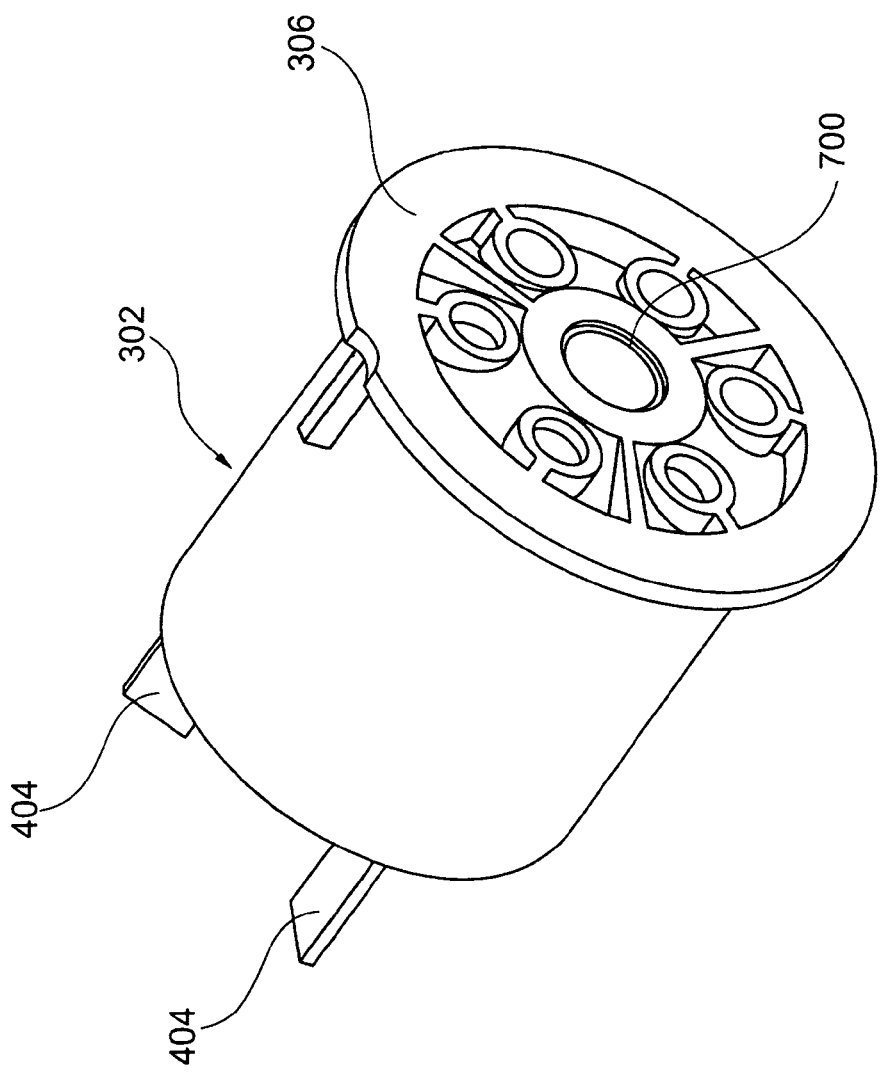
FIG. 7 shows a bottom part of the fluid dispenser of FIG. 3 with a plug as a sealing element sealingly closing a recess in a bottom surface of the bottom part.

FIG. 7 shows that the circular plate 306 on the lower surface of the bottom part 302 has an opening which is filled with a further injection molding part, i.e. a seal element 700. The hollow cylindrical seal element 700 can be inserted into the recess in the central portion of the circular plate 306 of the bottom part 302 and can be made of a material so that it can be penetrated by a pressure feed tip for supplying pressurized air to an interior of the casing 102.

Figure 8:
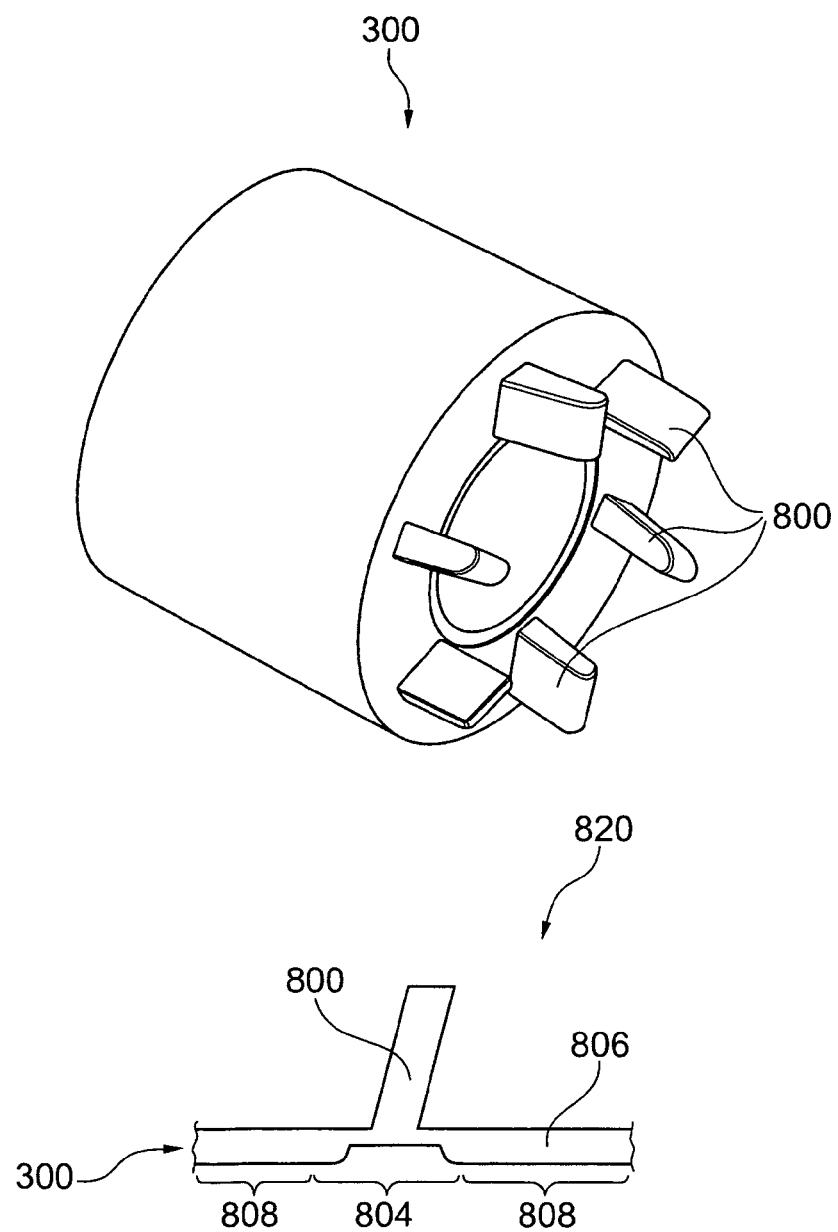
FIG. 8 shows a top part of the fluid cartridge of FIG. 3 with circumferentially arranged slanted plates as predetermined breaking structures for selectively enabling access to an interior of the fluid cartridge.

FIG. 8 shows a detailed view of the top part 300 and shows particularly the slanted plates 800 located in an upper surface of the top part 300. The slanted plates 800 are to be broken by bending upon applying a sufficient breaking force. As can be taken from a detail 820 in FIG. 8, an anchoring section 804 anchoring the predetermined breaking structures 800 in upper surface plate 806 of the top part 300 is selectively mechanically weakened, i.e. thinned locally, as compared to an environment 808 of the upper surface plate 806. Therefore, with a very small breaking force, the slanted plates 800 can be broken, thereby forming openings in the top plate of the top member 300.

Figure 9:
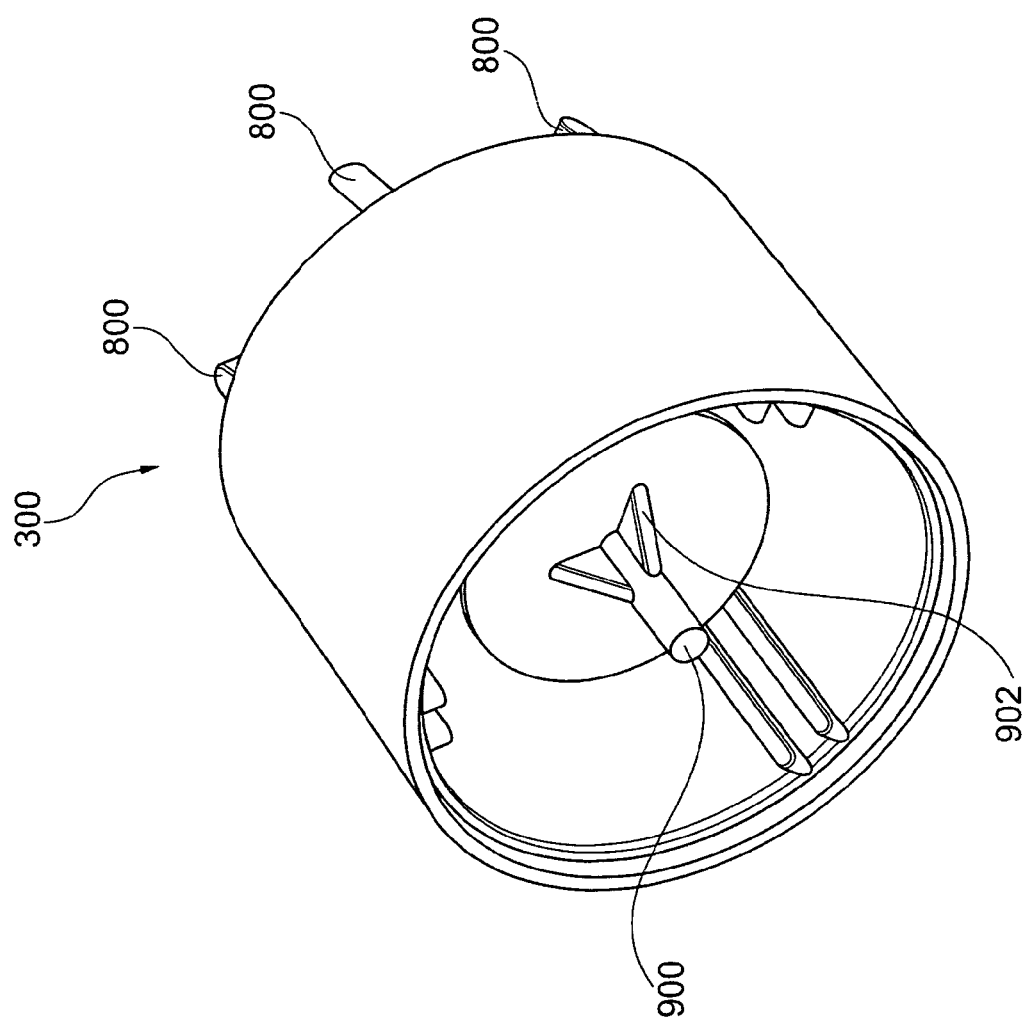
FIG. 9 shows another view of the top part of the fluid cartridge of FIG. 3 particularly showing an abutting pin as a deflector for fluid to generate aerosol-like fluidic particles.

FIG. 9 shows the internal construction of the top part 300. The top member 300 has in its interior volume a deflecting member 900 in the form of a deflecting pin at the end of a cylindrical body 902. The deflecting pin 900 is configured so that, upon ejecting the liquid through the further nozzle orifice 504, a liquid drop is divided into smaller liquid particles.

The material from which the fluid cartridges shown in FIG. 3 to FIG. 9 are made is preferably polyoxymethylene (POM) or a copolymer of acrylonitrile, butadiene and styrene. The latter material can also be called Polylac ABS®. The present inventors have made extensive experiments regarding appropriate materials and have concluded that these materials have good properties in terms of the suitability of being autoclaved, the suitability for ultrasonic welding and appropriate properties in terms of the formation of easily breakable predetermined breaking structures such as the one denoted with reference numeral 800 above.

Figure 10:
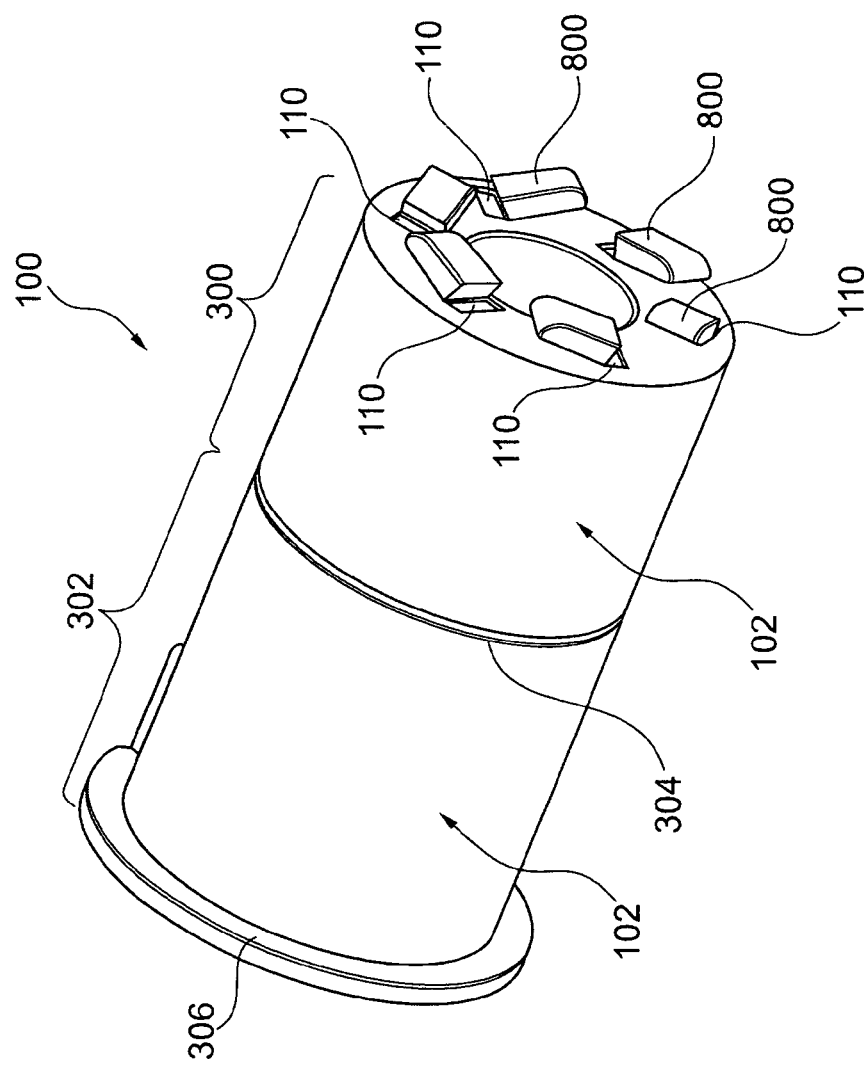
FIG. 10 shows a fluid cartridge according to an exemplary embodiment with broken predetermined breaking structures at a top part of the fluid cartridge enabling fluidic access to an interior of the fluid cartridge.

FIG. 10 shows a liquid cartridge 100 according to an exemplary embodiment of the invention which is also constituted by a bottom part 302 and a top part 300 welded together along an ultrasonic welding seam 304. The slanted plates 800 are broken now so as to form the fluidic channels 110 in the top surface of the cartridge 100 at openings formed due to the breaking. Breaking can be performed by pressing the slanted plates 800 against a planar counter element such as an underground or a plate. This breaking procedure may be performed manually by a user before using the fluid cartridge 100 for the first time or by a corresponding mechanism of a dispenser device.

Figure 11:
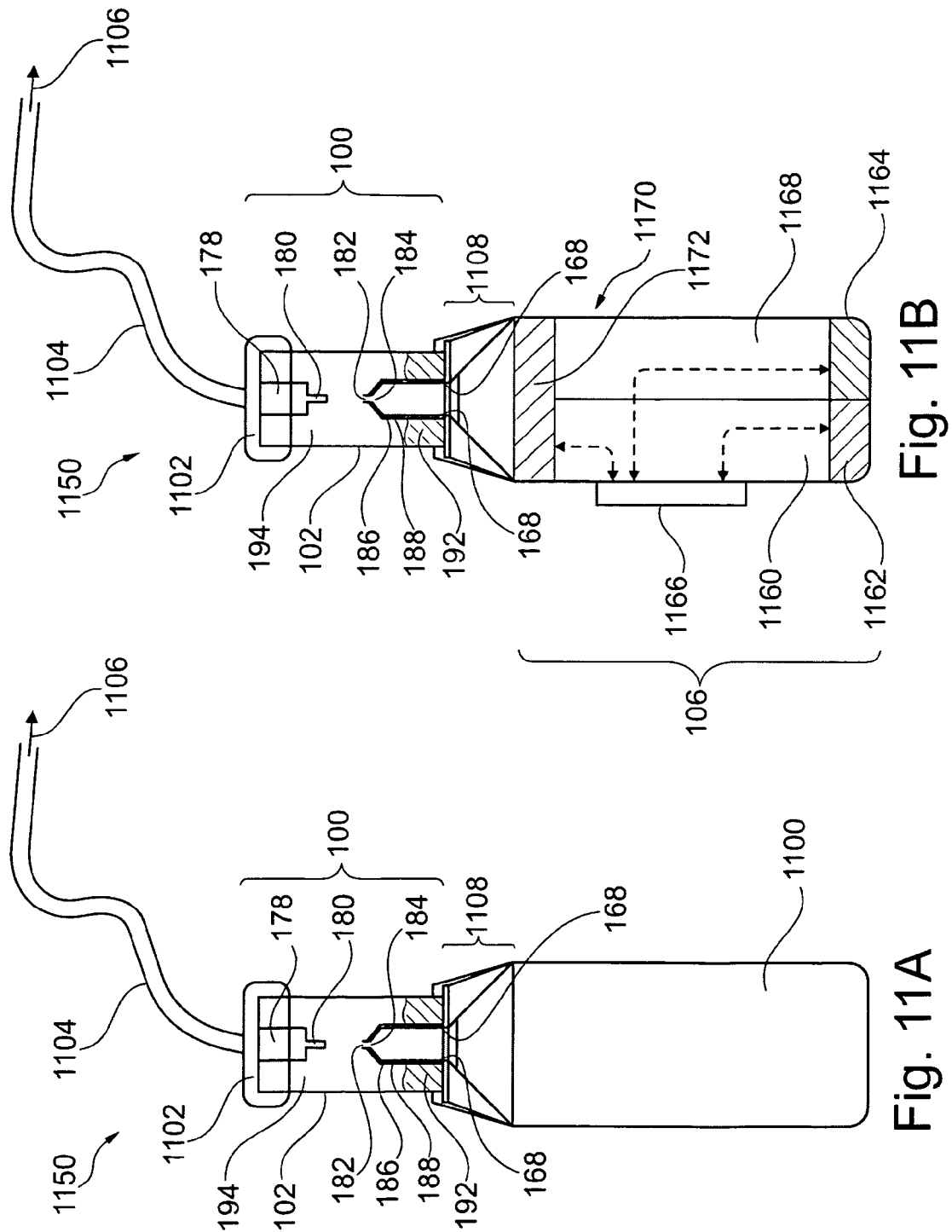
FIG. 11A shows a portable arrangement of an integrally formed combination of a pressurized medium accommodating container (such as a spray can or a gas bottle) and a fluid cartridge according to an exemplary embodiment of the invention.
FIG. 11B shows an arrangement of a pressurized medium accommodating container and a fluid cartridge according to another exemplary embodiment of the invention.

FIG. 11A shows a handheld arrangement 1150 configured as a portable device.

The arrangement 1100 comprises a liquid cartridge 100 as the one shown in FIG. 1. As in FIG. 1, a small opening 168 is provided between the stub 186 and a bottom of the casing 102. Therefore, fluid communication is possible via this small gap 168. In arrangement 1150, a user can plug the liquid container 100 onto an upper end of a spray can 1100 for providing a pressurized medium. The spray can 1100 can be filled with the pressurized medium so as to provide an overpressure (for instance 2 bar) towards an inner volume of the stub 188.

Upon attaching the liquid container 100 onto the spray can 1100, a connection or locking mechanism may be activated for connecting components 1100 and 100. For example, cooperating engagement means (such as grooves and protrusions) of components 1100, 100 may be brought into engagement upon carrying out such an attachment procedure. It is also possible to use a lever mechanism, a magnetic connection mechanism or the like to provide for such a connection. Furthermore, components 100, 1100 can be configured so that, upon connection, a pressure feed supply unit 106 may automatically penetrate the lower surface, for instance a membrane, of the casing 102 so that connection of the components 100, 1100 and formation of a pressurized medium supply path between the components 100, 1100 can be performed with one single hand movement.

FIG. 11A furthermore shows an adapter piece 1102 connecting an upper end portion of the liquid container 100 with a connection tube 1104. As indicated schematically with reference numeral 1106, at the end of the connection tube 1104 a respiratory mask may be foreseen so as to guide the dispensed particles towards a mouth and/or a nose of a human being or an animal wearing the respiratory mask (not shown). For example, the spray can 1100 may be for multiple use, whereas the liquid container 100 may be for a single use.

A further adapter section 1108 contains the connection elements (such as cooperating engagement elements) for connecting components 100, 1100.

As an alternative to the spray can 1100, any other pressurized medium accommodating container such as a gas bottle (particularly a nitrogen bottle) can be implemented in the embodiment of FIG. 11A.

FIG. 11B shows an arrangement 1150 according to another embodiment of the invention.

The arrangement 1150 in FIG. 11B is similar to arrangement 1150 in FIG. 11A but has another dispenser device 1170 with a pressure feed unit 106 comprising two separate pressurized medium chambers 1160, 1168 each accommodating a respective gas (as pressurized medium) and being configured for supplying a respective pressurized medium to the fluid in the liquid container 100 to thereby generate the particles, as described above.

A first temperature adjustment unit 1162 is configured for heating or cooling the pressurized medium in the first pressurized medium chamber 1160. A second temperature adjustment unit 1164 is configured for heating or cooling the pressurized medium in the second pressurized medium chamber 1168. By taking this measure, the respective pressurized medium may be heated or cooled to an appropriate temperature so as to properly fulfil its function in terms of fluid particle generation. Consequently, size and concentration of the particles may be adjusted precisely.

A regulating unit 1166 (such as a processor having a connected input/output unit as a user interface) is attached to an outer casing of the arrangement 1170 and allows a user to input control commands. The regulating unit 1166 is configured for regulating which of the separate pressurized medium chambers 1160, 1168 supplies its respective pressurized medium to the fluid in the liquid container 100. Also a mixing between different pressurized media is possible under control of the regulating unit 1166. Selection of one or more pressurized medium chambers 1160, 1168 supplying respective pressurized medium to the fluid cartridge may be made by correspondingly operating a valve 1172. The regulating unit 1166 is also configured for regulating the temperature of the pressurized medium in the pressurized medium chambers 1160, 1168. The regulation may be performed based on a sensor signal captured within the respective pressurized medium chambers 1160, 1168. Such a sensor signal may be indicative of an actual temperature, filling level, etc. in or of the respective pressurized medium chamber 1160, 1168. Hence, components (temperature adjustment units 1162, 1164, sensors, valve 1172, etc.) within the pressurized medium chamber 1160, 1168 may be communicatively coupled with the regulating unit 1166 for bidirectional signal exchange.

Figure 12:
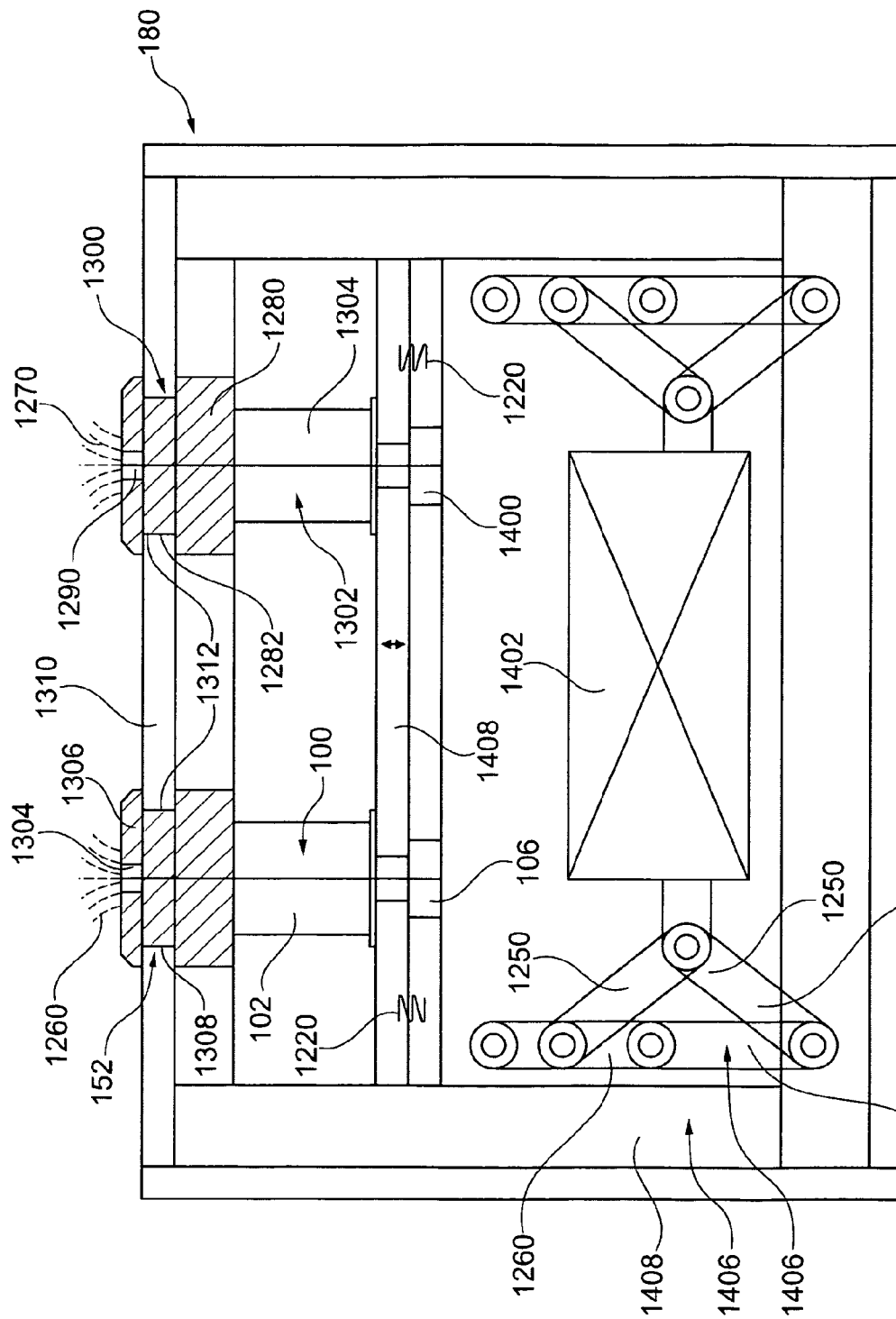
FIG. 12 shows a dispenser device according to an exemplary embodiment of the invention having mounted therein two fluid cartridges according to an exemplary embodiment of the invention.

FIG. 12 shows an arrangement 180 according to another exemplary embodiment of the invention.

In addition to the liquid cartridge 100 shown on the left-hand side of FIG. 12 accommodated in a liquid cartridge accommodation unit 152, the arrangement 180 comprises a further liquid cartridge accommodation unit 1300 accommodating a further liquid cartridge 1302 containing a further liquid in a further casing 1304. Furthermore, a further pressure feed unit 1400 is provided and configured for feeding the further liquid in the further casing 1304 with a further pressurized medium upon accommodating the further liquid cartridge 1302 in the further cartridge accommodation unit 1300. Thereby, further liquid nanoparticles may be generated on the right hand side of FIG. 12 which leave the further casing 1304 upon feeding the further liquid in the casing 102 with the pressure. Thus, a co-medication or co-treatment with two (or more) different liquids is possible with such an arrangement 180. The first nanofluidic particles are indicated with reference numeral 1260, whereas the second nanofluidic particles are indicated with reference numeral 1270.

As can be taken from FIG. 12 as well, the cartridge accommodation unit 152 comprises a separate fluid cartridge receptacle 1306 for receiving an upper end section of the liquid cartridge 100. The separate fluid cartridge receptacle 1306 furthermore has an engagement groove 1308. Accordingly, the cartridge accommodation unit 1300 comprises a separate fluid cartridge receptacle 1280 for receiving an upper end section of the liquid cartridge 1302. The separate fluid cartridge receptacle 1280 furthermore has an engagement groove 1282.

A mounting support 1310 in the form of a metal plate having certain recesses 1312 is configured for being engaged by the engagement grooves 1308, 1282, respectively for holding the liquid cartridge receptacles 1306, 1280, respectively for receiving the liquid cartridges 100, 1302, respectively. A respective through-hole 1304, 1290 in the respective liquid cartridge receptacle 1306, 1280 allows to expose the liquid conduits 110 of the liquid cartridges 100, 1302 to an environment when the liquid cartridge receptacles 1306, 1280 receive the liquid cartridges 100, 1302.

As shown in more detail in FIG. 1 and FIG. 2, the pressure feed unit 106 comprises a pressure feed pin 118 coupled to pressurized air reservoir 112 and is configured for penetrating a lower surface of the liquid cartridge 100 for feeding the liquid in casing 102 of the liquid cartridge 100 with the pressurized air. A corresponding provision is taken for the second cartridge 1302, see reference numeral 1400.

A linear motor 1402 is provided as a drive unit for driving the pressure supply pin 118 into the bottom surface of the fluid cartridge 100 and for driving the further pressure supply pin into the bottom surface of the further fluid cartridge 1302. For this purpose, the lower parts of the fluid cartridges 100, 1302 extending beyond the corresponding liquid cartridge receptacles 1306, 1280 can be forced to abut against a correspondingly movable (see arrow in FIG. 12) force transmission plate 1408. In other words, the linear motor 1210 may raise the movable force transmission plate 1408 towards the statically mounted mounting support 1310 to thereby drive the pressure supply pin 112 into the surface of the fluid cartridge 100 and simultaneously to drive the further pressure supply pin into the surface of the further liquid cartridge 1302.

Biasing elements 1220 such as springs which are shown only schematically in FIG. 12 exert a biasing force preventing the respective pressure supply pins 118 to enter into the respective liquid reservoirs 100, 1302. The linear motor 1402 provides a driving force to the force transmission plate 1408 via a guide mechanism 1406 for guiding the force transmission plate 1408 towards the mounting support 1310. FIG. 12 furthermore shows that the guide mechanism 1406 comprises a guide bearing 1408 cooperating with a knee lever 1410. FIG. 12 shows the knee lever 1410 in a first state in which it is angled (see reference numeral 1250) corresponding to a lowered position of the force transmission plate 1408 and in a second state in which it is in a straight configuration (see reference numeral 1260) corresponding to a raised position of the force transmission plate 1408.

Thus, a user may, for instance by pressing a button, initiate the raise of the mounting support 1408 towards a lower end of the liquid containers 100, 1302. Upon exerting a pressure to this bottom, the pressure supply pins 118 will penetrate the lower surface of the liquid containers 100, 1302 and will then be able to provide a pressure to the liquid contained therein. Consequently, this will trigger the spraying of nanoparticular liquid out of the containers 100, 1302.

Figure 13:
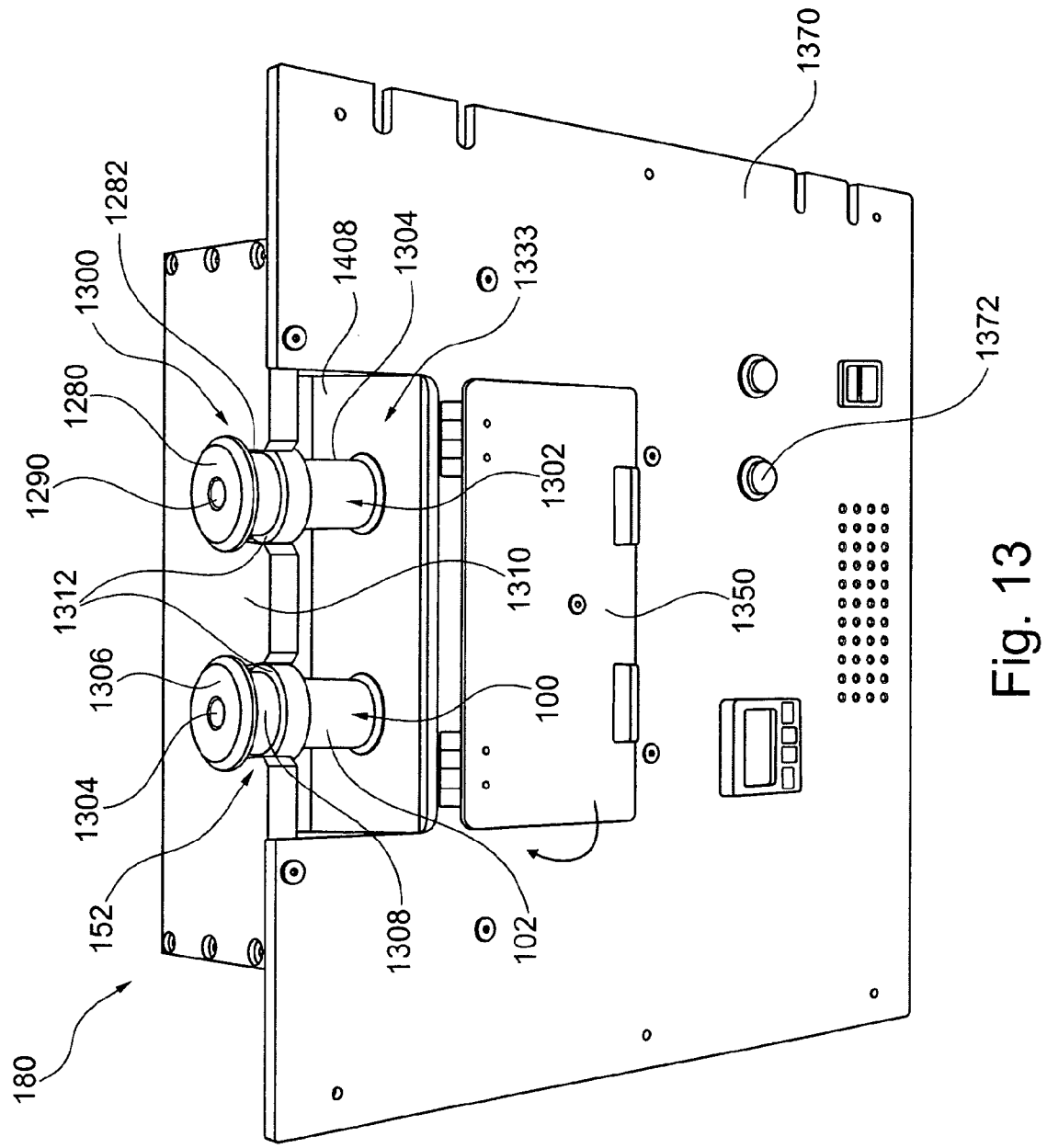
FIG. 13 to FIG. 17 show a dispenser device according to an exemplary embodiment of the invention in different operation modes.

FIG. 13 shows an image of arrangement 180 which corresponds to the schematic illustration of FIG. 12. FIG. 13 shows a front surface of the corresponding device. Firstly, a user inserts the liquid cartridges 100, 1302 into the metallic liquid cartridge receptacles 1306, 1280. Then, the combined elements 100, 1306 and 1302, 1280 are inserted into the corresponding recesses 1312 of the mounting support plate 1310. After this installation, a user may manually pivot (see arrow) a cover plate 1350 so as to close a mounting opening 1333 of a housing 1370 of the arrangement 180. A user may then start a dispensing procedure by pressing a button 1372. Upon closing the cover plate 1350, a detector (such as a magnetic sensor) may detect that the cover plate 1350 is closed now. For instance, a locking pin may then be guided into a lateral recess in the cover plate 1350 so as to lock the cover plate 1350 to the housing 1370. Upon pressing button 1372, the linear motor 1402 may automatically start to raise the force transmission plate 1408 until it abuts against a lower surface of the containers 100, 1302 to trigger gas supply.

Figure 14:
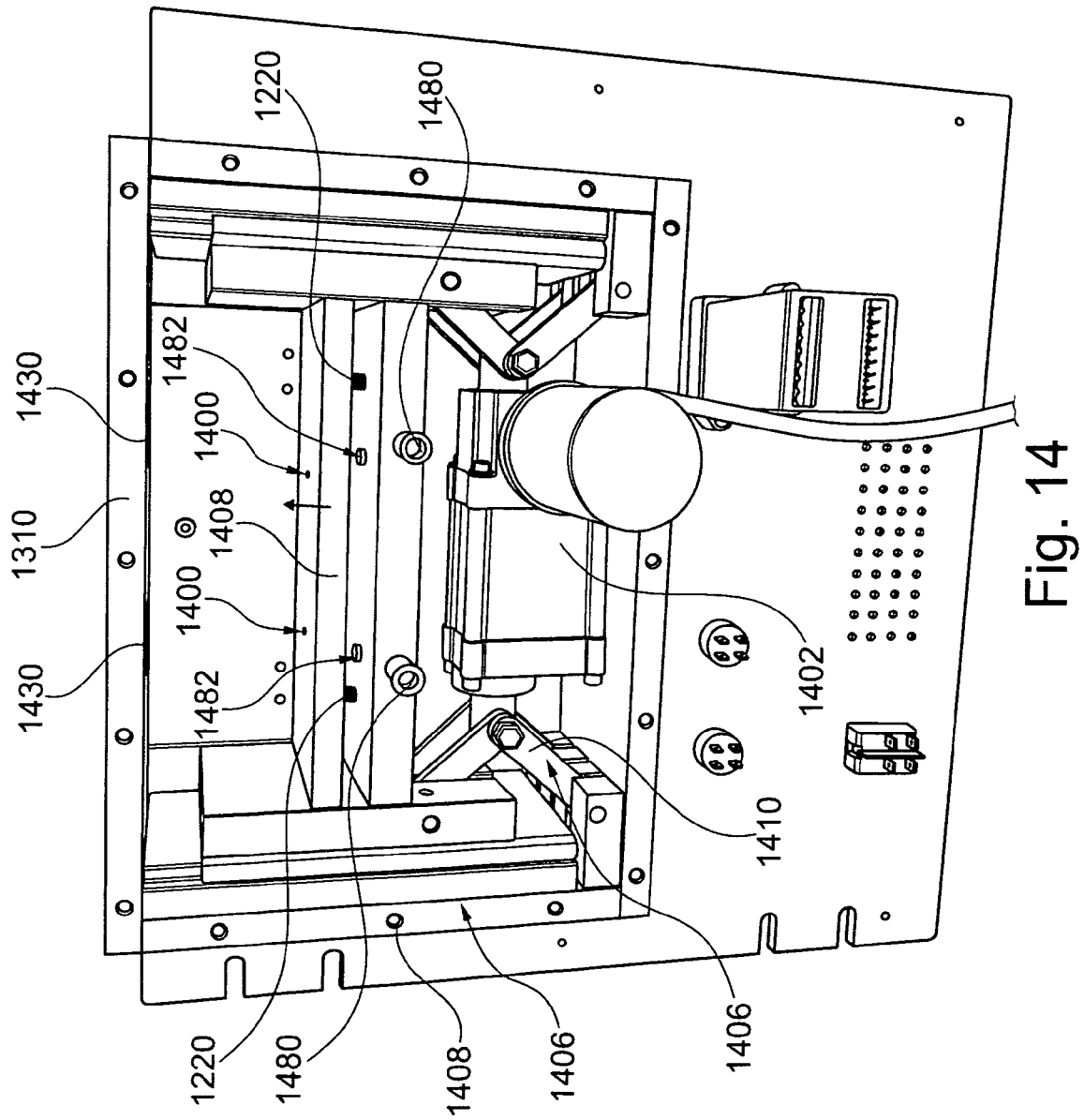

Now referring to FIG. 14 showing a rear side of the arrangement 180 of FIG. 13, pressurized air inlets 1480 are provided via which pressurized air can be supplied to pressure supply pins 1482. When fluid cartridges 102, 1300 (one or both) are mounted in respective recesses 1490 in the top plate 1404, and when the linear motor 1402 raises the force transmission plate 1408, the pressure supply pins 1482 may protrude through openings 1400 in the force transmission plate 1408 and may be driven into the fluid cartridges 100, 1302, respectively.

Figure 15:
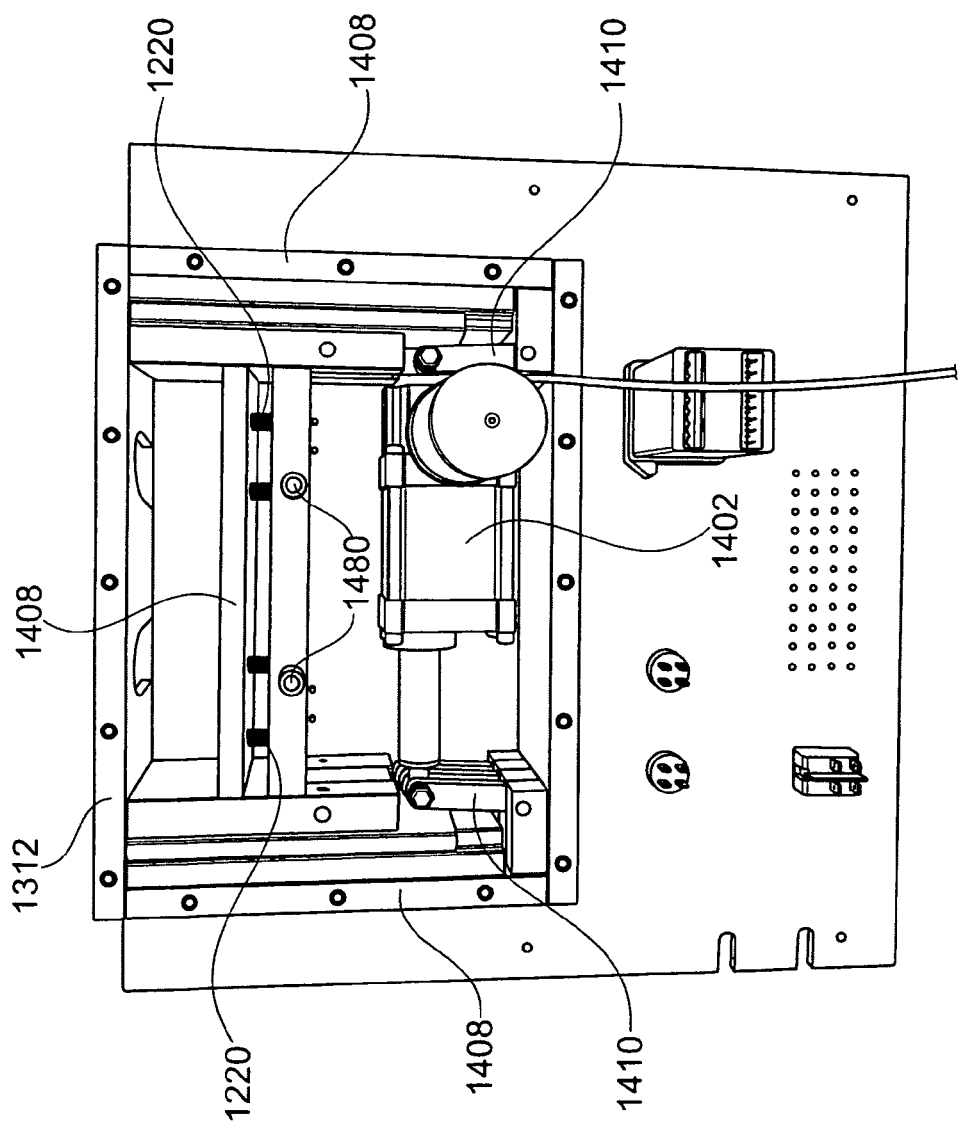

While FIG. 14 shows a state in which the knee lever 1410 is in an angled configuration, knee lever 1410 is in an almost straight configuration in FIG. 15.

Figure 16:
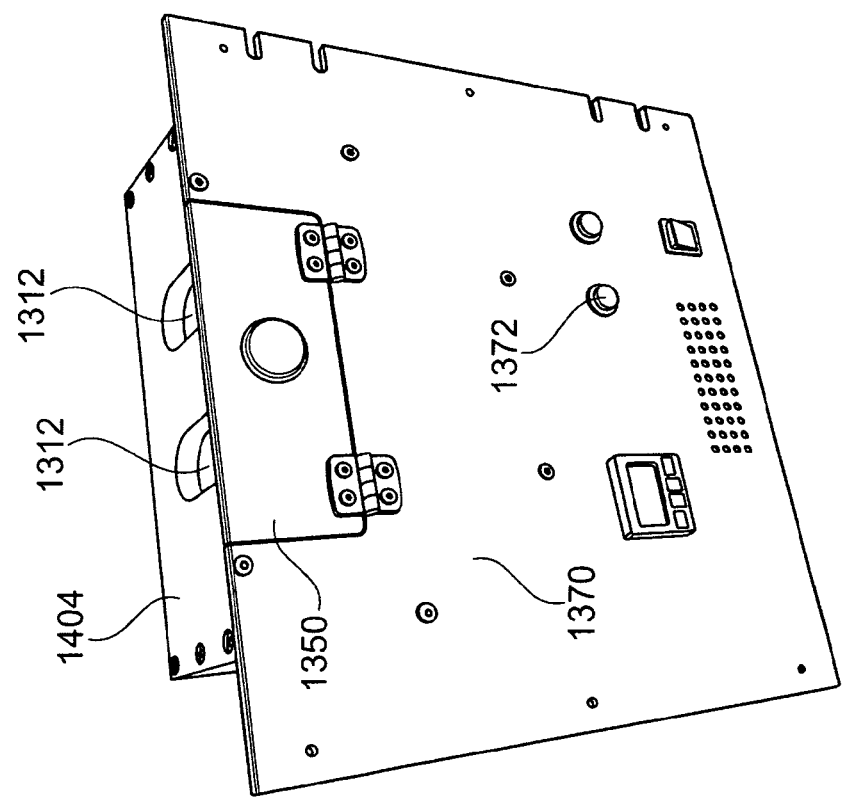

FIG. 16 shows a front view similar to FIG. 13 with the exception that the cover plate 1350 is now closed in FIG. 16.

Figure 17:
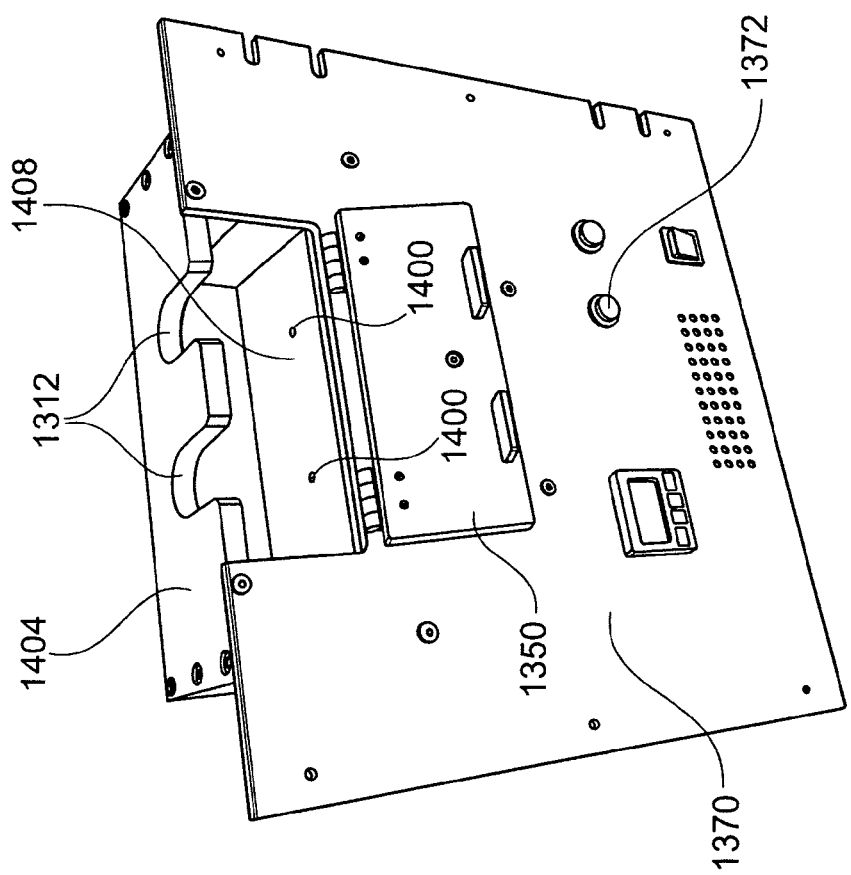

FIG. 17 shows a configuration similar to FIG. 16 with the cover plate 1350 being open.

Therefore, the system shown in FIG. 12, FIG. 13, FIG. 14 and FIG. 15 as well as FIG. 16 can be operated fully automatically without requiring a user to provide any contribution.

Figure 18:
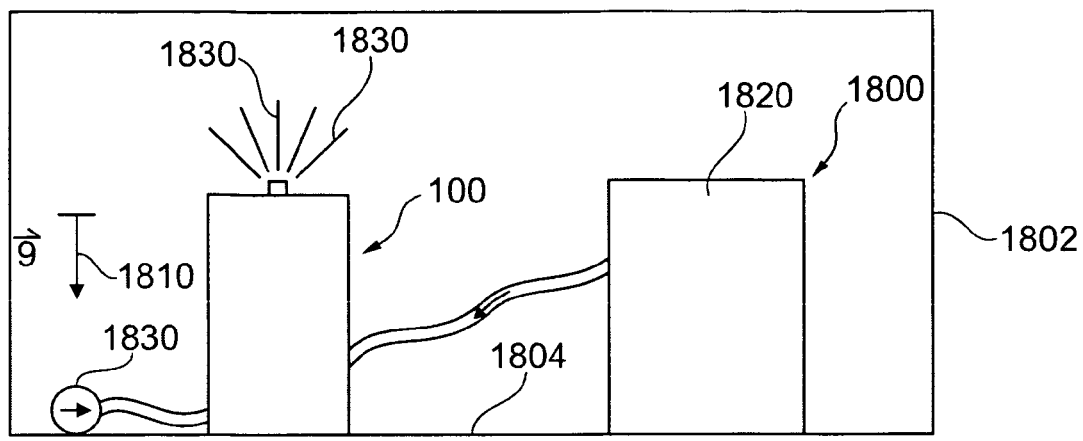
FIG. 18 shows a room with a dispenser device for disinfecting the room according to an exemplary embodiment of the invention.

FIG. 18 shows an arrangement 1800 according to another exemplary embodiment of the invention.

The arrangement 1800 is installed in a room 1802 (such as a hospital room) to be disinfected. A fluid dispenser 100 according to an exemplary embodiment of the invention which may be configured as described above is placed on a bottom or a floor 1804 of the room 1802. In the shown embodiment, the capacity of the liquid cartridge 100 is in a range between 1 l and 5 l. Using the influence of gravitation, see g-vector 1810, a disinfecting liquid such as citric acid is supplied from a container 1820 towards the fluid cartridge 100. Furthermore, pressurized gas such as nitrogen is applied from a pressurized gas source 1830 towards a lower section of the liquid cartridge 100. Consequently, citric acid 1830 as a disinfecting agent is sprayed out of an upper surface portion of the liquid container 100.

Figure 19:
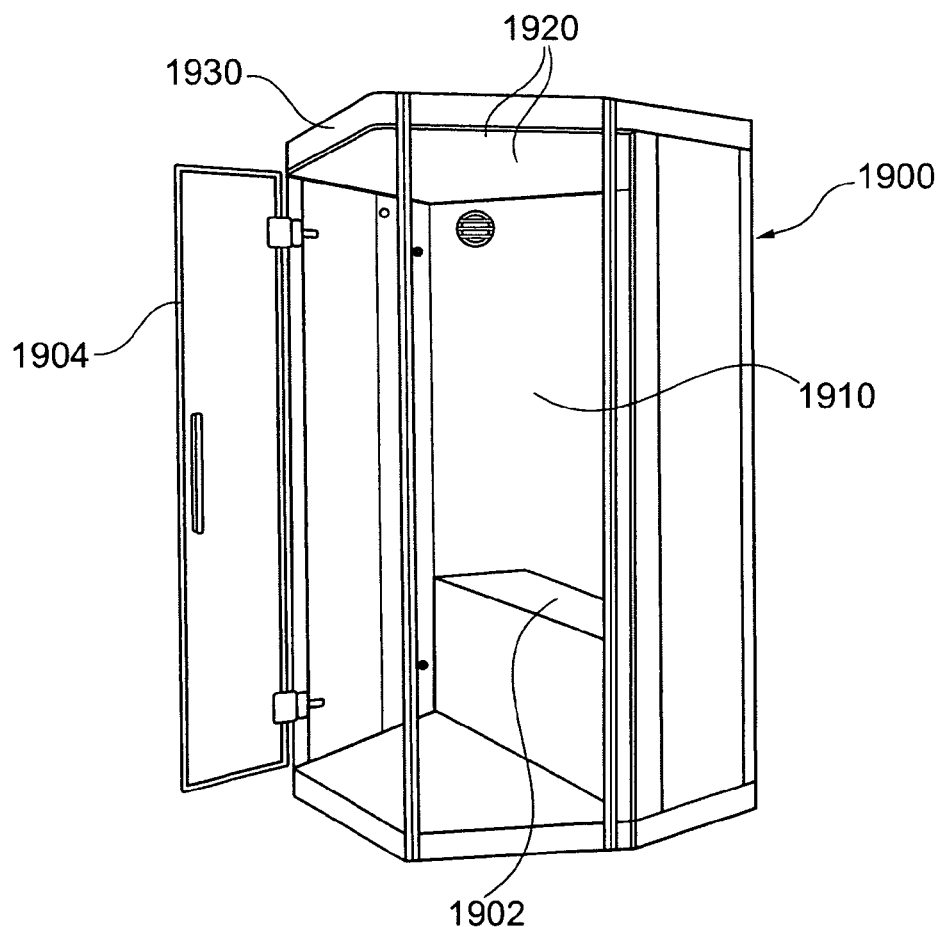
FIG. 19 shows a treatment cabin according to an exemplary embodiment of the invention accessible by a human being.

FIG. 19 shows a treatment cabin 1900 according to an exemplary embodiment of the invention having a seat for a human being denoted with reference numeral 1902. A door 1904 of the cabin 1900 can be closed. Nanoparticular liquid such as dead sea salt in an aqueous solution can be sprayed into an inner volume 1910 of the cabin 1900. It can be emitted via liquid cartridges 1920 integrated in a ceiling 1930 of the cabin 1900.

Figure 20:
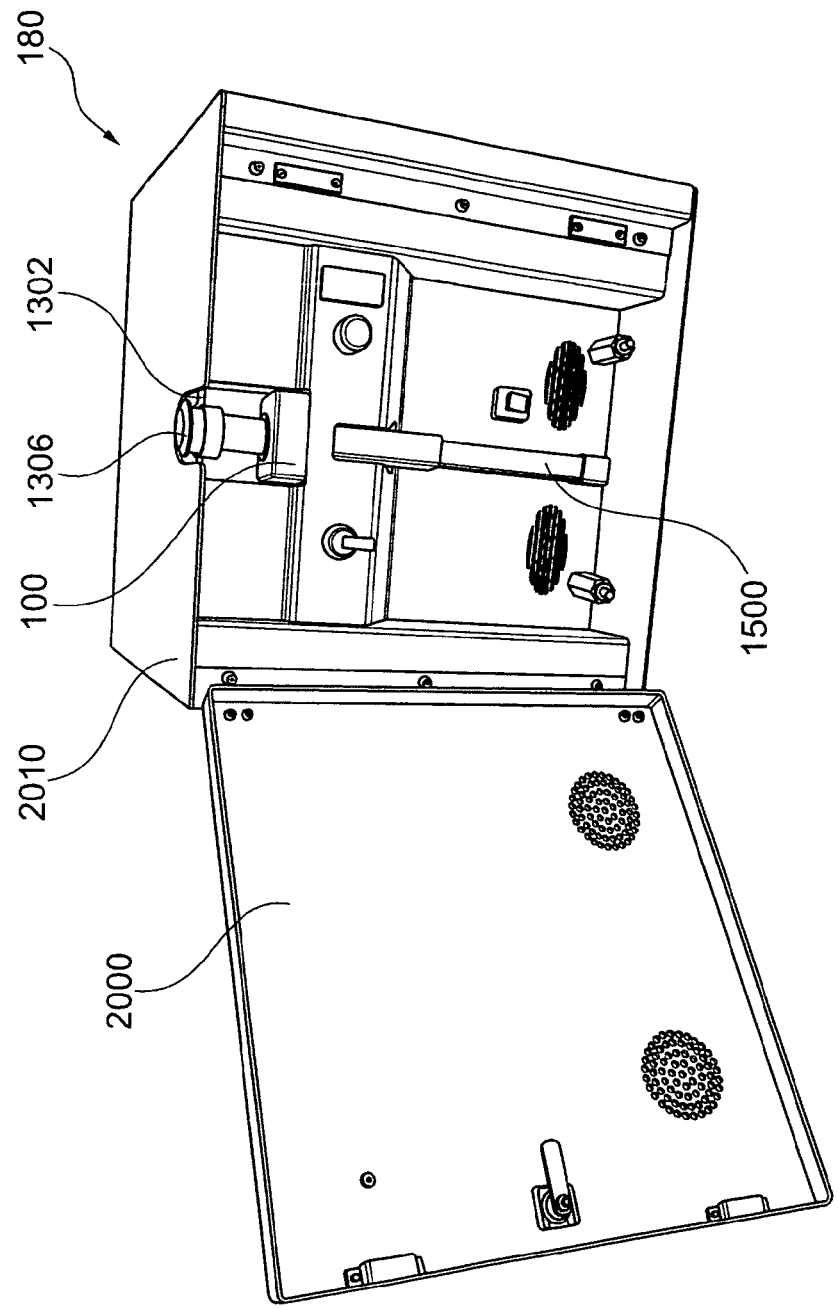
FIG. 20 shows a dispenser device according to an exemplary embodiment of the invention with a manually operable lever mechanism.

An arrangement 180 shown in FIG. 20 has a pivotable front door 2000 which is opened in the shown configuration. A liquid cartridge 100 mounted in a liquid cartridge receptacle 1306 is received in a recess 1302 of a receiving plate 2010. By manually pivoting a lever 1500 by a user, a pressure feed pin can be guided through a lower surface of the liquid cartridge 100. After closing the door 2000 a user may start the dispensing procedure.

Figure 21:
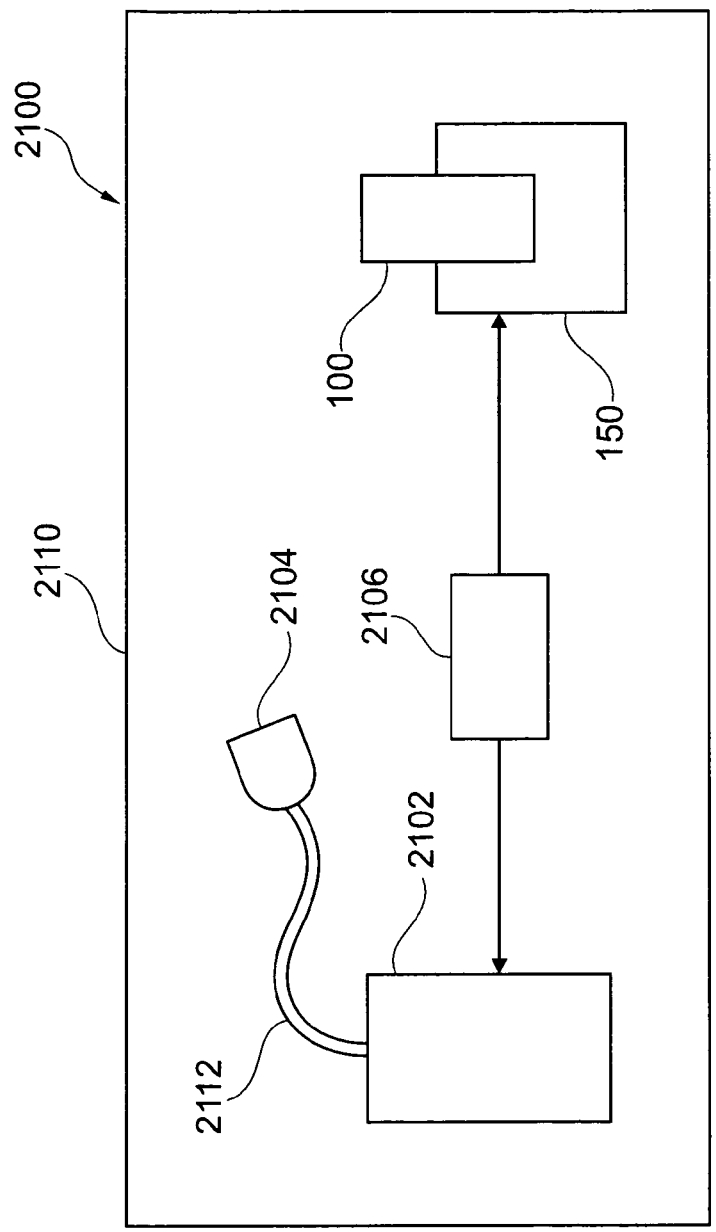
FIG. 21 shows an arrangement of a fluid cartridge and a dispenser device one the one hand and a further fluid particle source connected to a respiratory mask on the other hand according to an exemplary embodiment of the invention.

FIG. 21 shows an arrangement 2100 of a fluid cartridge 100 and a dispenser device 150 one the one hand and a further fluid particle source 2102 connected to a respiratory mask 2104 on the other hand according to an exemplary embodiment of the invention. The arrangement 2100 is located within a treatment chamber 2110 in which a human user can be present.

The respiratory mask 2104 is fluidically connected to the particle source 2102 via a tube 2112 so as to guide particles towards a mouth and/or a nose of the user wearing the respiratory mask 2104. The particle source 2102 is provided separately from the fluid cartridge 100 and the dispenser device 150. Both, particle source 2102 and system of fluid cartridge 100 and dispenser device 150 can be controlled by a common control unit 2106 such as a processor.

It should be noted that the term "comprising" does not exclude other elements or steps and the "a" or "an" does not exclude a plurality. Also elements described in association with different embodiments may be combined.

It should be also be noted that reference signs in the claims shall not be construed as limiting the scope of the claims.

Implementation of the invention is not limited to the preferred embodiments shown in the figures and described above. Instead, a multiplicity of variants are possible which use the solutions shown and the principle according to the invention even in the case of fundamentally different embodiments.

The invention claimed is:

1. A fluid cartridge for dispensing a fluid, the fluid cartridge comprising:
   a casing for accommodating the fluid, the casing comprising a top part;
   a pressure feed interface configured for being coupled to a pressure feed unit for feeding the fluid in the casing with pressurized medium;
   a fluid dispensing unit configured for generating particles upon feeding the fluid in the casing with pressurized medium;
   a fluidic path in the casing being opened or openable for enabling the particles to leave the casing through the fluidic path;
   wherein the top part has at least one predetermined breaking structure configured for being broken by applying a breaking force so as to open the fluidic path in the casing upon breaking; and
   wherein the at least one predetermined breaking structure comprises at least one slanted plate located in an upper surface of the top part so as to be broken by bending or kinking the at least one slanted plate upon applying the breaking force.

2. The fluid cartridge of claim 1, wherein the casing further comprises a bottom part, the bottom part and the top part being integrally connected to one another.

3. The fluid cartridge of claim 2,
   wherein the top part has at least one recess as the fluidic path;
   wherein the fluid cartridge further comprises a peelable layer being removable from the top part by peeling so as to expose the fluidic path.

4. The fluid cartridge of claim 1, wherein an anchoring section anchoring the at least one predetermined breaking structure in an upper surface of the top part is selectively mechanically weakened as compared to an environment of the upper surface.

5. The fluid cartridge of claim 1, wherein the casing comprises or consists of one of the group consisting of:
   a thermoplastic material;
   elastomeric material;
   polyoxymethylene;
   a copolymer of Acrylonitrile, Butodiene, and Styren; and
   $(C_3H_3N, C_4H_6, C_8H_8)_x$.

6. The fluid cartridge of claim 1, wherein the fluid cartridge comprises the pressure feed unit.

7. The fluid cartridge of claim 6, wherein the pressure feed unit is a pressurized medium accommodating unit comprising the pressurized medium, wherein the casing is mounted on the pressurized medium accommodating unit so that the pressure feed interface is supplyable with the pressurized medium from the pressurized medium accommodating unit.

8. The fluid cartridge of claim 6, comprising one of the following features:
   the casing is detachably mountable on the pressure feed unit; or
   the casing is integrally formed with the pressure feed unit.

9. The fluid cartridge of claim 1, comprising a cartridge data carrier wherein the cartridge data carrier carries information assigned to the fluid cartridge and being readable by a reader unit.

10. The fluid cartridge of claim 1, wherein the casing accommodates the fluid, wherein the fluid particularly comprises at least one of the group consisting of hyaluronic acid, a mixture of hyaluronic acid and sodium chloride solution, olive oil, an essential oil, dead sea salt, dead sea salt with L-ascorbate, evening primpose oil, black cumin oil, aloe vera, algae extract, cucumber, avocado oil, panthenol, an oil-coated active agent, a human medication, a veterinary medication, a wellness preparation, citric acid, ozone, and any combination of the above fluids.

11. A method of dispensing a fluid, the method comprising:
    accommodating the fluid in a casing;
    coupling a pressure feed interface of the casing to a pressure feed unit to thereby feed the fluid in the casing with pressurized medium;
    generating particles in the casing upon feeding the fluid in the casing with pressurized medium;
    opening a fluidic path of the casing by breaking at least one predetermined breaking structure in a top part of the casing, wherein the at least one predetermined breaking structure comprises at least one slanted plate located in an upper surface of the top part so as to be broken by bending or kinking the at least one slanted plate upon applying a breaking force;
    providing the fluidic path in the casing being open for enabling the particles to leave the casing through the fluidic path.

12. A dispenser device for dispensing a fluid from a fluid cartridge the dispenser device comprising:
    a cartridge accommodation unit configured for accommodating the fluid cartridge;
    a pressure feed unit configured for feeding the fluid in a casing of the fluid cartridge with a pressurized medium upon accommodating the fluid cartridge in the cartridge accommodation unit to thereby generate particles leaving the casing through a fluidic path in the casing upon feeding the fluid in the casing with the pressurized medium;
    the fluidic path in the casing being openable by breaking at least one predetermined breaking structure, wherein the at least one predetermined breaking structure comprises at least one slanted plate located in an upper surface of a top part of the casing so as to be broken by bending or kinking the at least one slanted plate upon applying the breaking force.

13. The dispenser device of claim 12, wherein the dispenser device, comprises a read and/or write unit configured for reading data from and/or writing data to a cartridge data carrier of the fluid cartridge upon accommodating the fluid cartridge at the cartridge accommodation unit.

14. The dispenser device of claim 12, further comprising:
    a further cartridge accommodation unit configured for accommodating a further fluid cartridge having a further fluid in a further casing;
    a further pressure feed unit configured for feeding the further fluid in the further casing with a further pressurized medium upon accommodating the further fluid cartridge in the further cartridge accommodation unit to thereby generate further particles leaving the further casing upon feeding the further fluid in the further casing with the further pressurized medium.

15. The dispenser device of claim 12, wherein the pressure feed unit comprises a pressure supply pin coupled to a pressure medium reservoir and being configured for penetrating a surface of the fluid cartridge for feeding the pressurized medium to the fluid in a casing of the fluid cartridge, and a drive unit configured for driving the pressure supply pin into the surface of the fluid cartridge.

16. The dispenser device of claim 12, wherein the pressure feed unit comprises a pressure supply pin coupled to a pressure medium reservoir and being configured for penetrating a surface of the fluid cartridge for feeding the pressurized medium to the fluid in a casing of the fluid cartridge, and a lever mechanism actuable by a user, wherein the pressure supply pin penetrates the surface of the fluid cartridge upon actuating the lever mechanism.

17. A method of dispensing a fluid from a fluid cartridge, the method comprising:

accommodating the fluid cartridge in a cartridge accommodation unit;

feeding the fluid in the casing with a pressurized medium upon accommodating the fluid cartridge in the accommodation unit to thereby generate particles leaving the casing upon feeding the fluid in the casing with the pressurized medium.

18. An arrangement for dispensing a fluid, the arrangement comprising:

a fluid cartridge having a casing for accommodating the fluid;

a pressure feed interface configured for being coupled to a pressure feed unit for feeding the fluid in the casing with pressurized medium;

a fluid dispensing unit configured for generating particles upon feeding the fluid in the casing with pressurized medium;

a fluidic path in the casing being opened or openable for enabling the particles to leave the casing through the fluidic path;

the fluidic path in the casing being openable by breaking at least one predetermined breaking structure, wherein the at least one predetermined breaking structure comprises at least one slanted plate located in an upper surface of a top part of the casing so as to be broken by bending or kinking the at least one slanted plate upon applying the breaking force;

a dispenser device having a cartridge accommodation unit configured for accommodating the fluid cartridge;

a pressure feed unit configured for feeding the fluid in a casing of the fluid cartridge with a pressurized medium upon accommodating the fluid cartridge in the cartridge accommodation unit to thereby generate particles leaving the casing through a fluidic path in the casing upon feeding the fluid in the casing with the pressurized medium.

19. The arrangement of claim 18, wherein the fluid cartridge comprises a tamper-proof feature being indicative of an origin of the fluid cartridge;

wherein the dispenser device comprises a tamper-proof verification unit corresponding to the tamper-proof feature and being configured for verifying whether a fluid cartridge accommodated by the dispenser device has a tamper-proof feature being indicative of an approved origin of the fluid cartridge;

wherein the dispenser device is further configured to enable generation of particles only upon successful verification that the fluid cartridge has the tamper-proof feature.

20. A method of using an arrangement of claim 18 for treating a physiological subject by the dispensed fluid, the dispensed fluid particularly being a non-medical preparation.

21. The method of claim 20, wherein the arrangement is configured as a portable device dimensioned so that a human being, as the physiological subject, is treated with the particles, particularly fluid particles, by manually handling the device.

22. The method of claim 20, wherein the arrangement is used for disinfecting a room.

* * * * *